(12) United States Patent
Shen

(10) Patent No.: US 7,582,602 B2
(45) Date of Patent: Sep. 1, 2009

(54) HIRULOG-LIKE PEPTIDE AND GENE THERAPY

(76) Inventor: Garry X. Shen, 631 Drake Centre, Winnipeg Manitoba (CA) R3T 5V4

( * ) Notice: Subject to any disclaimer, the term of this patent is extended or adjusted under 35 U.S.C. 154(b) by 0 days.

(21) Appl. No.: 10/872,254

(22) Filed: Jun. 18, 2004

(65) Prior Publication Data

US 2004/0229806 A1 Nov. 18, 2004

Related U.S. Application Data

(63) Continuation of application No. 09/822,882, filed on Mar. 30, 2001, now abandoned.

(60) Provisional application No. 60/193,114, filed on Mar. 30, 2000.

(51) Int. Cl.
*A61K 38/00* (2006.01)
*A01N 37/18* (2006.01)

(52) U.S. Cl. ............................. 514/2; 514/12; 530/300

(58) Field of Classification Search ..................... 514/2, 514/12; 530/300
See application file for complete search history.

(56) References Cited

FOREIGN PATENT DOCUMENTS

WO         WO 91/02750      *   3/1991

OTHER PUBLICATIONS

Rajagopal et al., Coronary restenosis: a review of mechanisms and management. The American Journal of Medicine vol. 115, Issue 7, Nov. 2003, pp. 547-553.*
Chen et al., Hirulog-like peptide reduces restenosis and expression of tissue factor and transforming growth factor-beta in carotid artery of atherosclerotic rabbits. Atherosclerosis. Jul. 2003;169(1):31-40.*
Thrombin and antithrombotics Semin Thromb Hemost; 1998; 24(2):87-91 Fenton, JW; et al.
Protein-C: Biochemistry, Physiology, and Clinical Implications Blood; vol. 62, No. 6 (Dec.), 1983: pp. 1155-1158 Charles T. Esmon.
Ethanol Inhibits Thrombin-induced Secretion of the Contents of Human Platelet Dense and α-Granules and Lysosomes Thromb Haemost; 1998; 80: 662-7 A. Nguyen; et al.
The Biology of Platelet-Derived Growth Factor Cell; Jul. 18, 1986;46(2):155-69 Ross R, et al.
The Role of Secondary Growth Factor Production in Thrombin-induced Proliferation of Vascular Smooth Muscle Cells Semin Thromb Hemost; 1998;24(2):145-50 Stouffer GA, Runge MS.
"Thrombin" Receptor-directed Ligand Accounts for Activation by Thrombin of Platelet Phospholipase C and Accumulation of 3-Phosphorylated Phosphoinositides The Journal of Biological Chemistry; vol. 266, No. 28, Issue of Oct. 5, pp. 18435-18438, 1991 Ru-song Huang, et al.
cDNA cloning and expression of a hamster α-thrombin receptor coupled to $Ca^2$ mobilization FEBS 10062; vol. 288, No. 1,2, 123-128, Aug. 1991 Ulla B. Rasmussen, et al.

Molecular cloning of a functional thrombin receptor reveals a novel proteolytic mechanism of receptor activation. Cell; Mar. 22, 1991;64(6):1057-68 Vu TK, et al.
Transcellular signaling and pharmacological modulation of thrombin-induced production of plasminogen activator inhibitor-1 in vascular smooth muscle cells. Semin Thromb Hemost; 1998;24(2);151-6 Shen GX, et al.
G proteins and phospholipase C mediate thrombin-induced generation of plasminogen activator inhibitor-1 from vascular smooth muscle cells. J Vasc Res.; Mar.-Apr. 1997;34(2):82-9 Ren S, et al.
Guidelines for Percutaneous Transluminal Coronary Angioplasty A Report of the American College of Cardiology/American Heart Association Task Force on Assessment of Diagnostic and Therapeutic Cardiovascular Procedures (Subcommittee on Percutaneous Transluminal Coronary Angioplasty) ACC/AHA Task Force Report ACC; vol. 12, No. 2 Aug. 1988;529-45.
Intracoronary stenting compared with conventional therapy for abrupt vessel closure complicating coronary angioplasty: a matched case-control study J Am Coll Cardiol, 1993; 21:866-875 AM Lincoff et al.
A cascade model for restenosis. A special case of atherosclerosis progression. Circulation. Dec. 1992;86(6 Suppl):III47-52 Libby P et al.
Prevention of stenosis after vascular reconstruction: pharmacologic control of intimal hyperplasia—a review. J Vasc Surg. Jun. 1991;13(6):885-91. Clowes AW, Reidy MA.
A Call for Provisional Stenting: The Balloon is Back! Circulation, 1998;97;1298-1305 Craig R. Narins et al.
Restenosis- An Assessment of Factors Important in Arterial Occlusion SM Schwartz, MA Reidy Atherosclerosis and Coronary Heart Disease Lippincott Raven Publishers, Philadelphia 1996. Chap 39:701-12 V. Furster et al.
Vascular Complications after balloon and new device angioplasty Circulation, Oct. 1993;88(4 Pt 1):1569-78 Popma JJ et al.
Impaired Arterial Neointima Formation in Mice with Disruption of the Plasminogen Gene J. Clin. Invest. vol. 99, No. 2, Jan. 1997, 200-208 Peter Carmeliet et al.
Postangioplasty restenosis: Platelet activation and the coagulation-fibrinolysis system as possible factors in the pathogenesis of restenosis American Heart Journal, Apr. 1997, vol. 133, No. 4 Sugao Ishiwata et al.
Antithrombotics in interventional cardiology: optimizing treatment and strategies Am J Cardiol. Sep. 10, 1998;82(5B):25L-28L Ischinger TA.

(Continued)

*Primary Examiner*—Maria Leavitt
(74) *Attorney, Agent, or Firm*—Michael R. Williams; Ade & Company Inc.

(57) ABSTRACT

There is provided a hirulog-like peptide. Also provided is the treatment of vascular restenosis including the steps of administering an effective amount of a hirulog-like peptide in a pharmaceutically acceptable carrier whereby administration prevents vascular restenosis. A pharmaceutical composition including a hirulog-like peptide and a pharmaceutically acceptable carrier is also provided. A vector expressing a hirulog-like peptide is also provided. Also provided by the present invention is a method of treating a patient with vascular restenosis by introducing to the patient an amount of a sequence encoding a hirulog-like peptide sufficient to prevent vascular restenosis.

3 Claims, 4 Drawing Sheets

OTHER PUBLICATIONS

Circulating cell adhesion molecules and endothelial markers before and after transluminal antioplasty in peripheral arterial occlusive disease Atherosclerosis, Jan. 1999;142(1)193-200 Tsakiris DA et al.

Coronary atherectomy. Clinical, angiographic, and histological findings and observations regarding potential mechanisms. Circulation. Jul. 1990;82(1):69-79 Comment in: Circulation. Jul. 1990;82(1):305-7.

Molecular genetics of the fibrinolytic and coagulation systems in haemostasis, thrombogenesis, restenosis and atherosclerosis. Curr Opin Lipidol. Apr. 1997;8(2):118-25 Carmeliet P, Collen D.

A rationale for targeting antithrombotic therapy at the vessel wall: improved antithrombotic effect and decreased risk of bleeding Wien Klin Wochenschr. Feb. 12, 1999;111(3):81-9 Buchanan MR, Brister SJ.

Pharmacological Approaches for the Prevention of Restenosis After Percutaneous Coronary Intervention Progress in Cardiovascular Diseases, Vo. 40, No. 2 (Sep./Oct.), 1997, pp. 141-158 Lefkovits J and Topol EJ.

Trapidil (triazolopyrimidine), a platelet-derived growth factor antagonist, reduces restenosis after percutaneous transluminal coronary angioplasty. Results of the randomized, double-blind STARC study. Studio Trapidil versus Aspirin nella Restenosi Coronarica Circulation, Dec. 1994;90(6):2710-5 Maresta A et al.

Propucol inhibits neointimal thickening and macrophage accumulation after balloon injury in the cholesterol-fed rabbit Proc. Natl. Acad. Sci. USA Vol. 89, pp. 11312-11316, Dec. 1992 Medical Sciences Ferns G. A. A. et al.

Clinical trials of primary and secondary prevention of thrombosis and restenosis Thromb Haemost. Jul. 1995;74(1)377-81 Vermylen J.

Effectiveness of hirulog in reducing restenosis after balloon angioplasty of atherosclerotic femoral arteries in rabbits J Vasc Res. Jul.-Aug. 1996;33(4):308-14 Sarembock IJ et al.

Prolonged Thrombin Inhibition Reduces Restenosis After Balloon Angioplasty in Porcine Coronary Arteries Circulation. 1998;97;581-588 Gallo R et al.

Effects of Platelet Glycoprotein IIb/IIIa receptor Blockade by a Chimeric Monoclonal Antibody (Abcisimab) on Acute and Six-Month Outcomes After Percutaneous Transluminal Coronary Angioplasty for Acute Myocardial Infarction AM J Cardiol 1996;77:1045-1051 Lefkovits J et al.

Effects of β3-Integrin Blockade (c7E3) on the Response to Angioplasty and Intra-Arterial Stenting in Atherosclerotic Nonhuman Primates Arterioscler. Thromb. Vasc. Biol. 1998;18;1730-1737 Deitch J et al.

Use of abciximab (c7E3 Fab, ReoPro) as an adjunct to balloon angioplasty. Can J Cardiol. Feb. 1999;15(2):201-7 McGregor M, Brophy JM.

Treatment of Venous Thromboembolism with Low Molecular Weight Heparins Hematol Oncol Clin North Am. Oct. 1992;6(5):1095-103 Hull RD, Pineo GF.

Study design of the International Stroke Trial (1ST), baseline data, and outcome in 984 randomised patients in the pilot study. Journal of Neurology, Neurosurgery, and Psychiatry 1996;60:371-376 International Stroke Trial Pilot Study Collaborative Group.

Clot-bound Thrombin is protected by inhibition by Heparin-Antithrombin III but is susceptible to inactivation by Antithrombin III-independent inhibitors. J Clin. Invest. vol. 86, Aug. 1990, 385-391 Weitz J. et al.

Heparin Selectively Inhibits The Transcription of Tissue-type Plasminogen Activator in Primate Arterial Smooth Muscle Cells during Mitogenesis The Journal of Biological Chemistry vol. 267, No. 5, Issue of Feb. 15, pp. 3438-3444, 1992 Y.P. Tina Au et al.

New antithrombotic agents The Lancet, vol. 353, Apr. 24, 1999 pp. 252:1431-36 Jack Hirsh, Jeffrey I Weitz.

Usefulness of Subcutaneous Low Molecular Weight in Heparin (Ardeparin) for Reduction of Restenosis After Percutaneous Transluminal Coronary Angioplasty Am J Cardiol 1999;83:1524-1529 Lawrence W. Gimple et al.

Comparative Properties of two clinical preparations of recombinant human tissue-type plasminogen activator in patients with acute myocardial infarction Am Coll Cardiol 1987;9:599-607.

Reperfusion in acute myocardial infarction Mayo Clin Proc. Apr. 1990;65(4):549-64 Lavie CJ et al.

Cloning and expression of a cDNA coding for the anticoagulant hirudin from the bloodsucking leech, Hirudo Medicinalis Proc. Natl. Adad. Sci. USA. vol. 83, pp. 1084-1088, Feb. 1986 Medical Sciences R P. Harvey et al.

A comparison of Hirudin with Heparin in the Prevention of Restenosis After Coronary Angioplasty N. Engl J Med 1995:333:757-63 Patrick W. Serruys et al.

Early Plus Delayed Hirudin Reduces Restenosis in the Atherosclerotic Rabbit More than Early Administration Alone: Potential Implications for Dosing of Antithrombin Agents Circulation 1998;98;2301-2306 Leonard M. Thome et al.

Local adenoviral-mediated expression of recombinant hirudin reduces neointima formation after arterial injury Nat Med. Mar. 1996;2(3):293-8 Rade JJ et al.

Safety and Efficacy of recombinant hirudin (CGP 39 393) versus heparin in patients with stable angina undergoing coronary angioplasty Circulation 1993;88;2058-2066 AA van den Bos et al.

Recombinant hirudin for unstable angina pectoris. A multicenter, randomized angiographic trial Circulation 1994;89;1557-1566 EJ Topol et al.

A pilot trial of recombinant desulfatohirudin compared with heparin in conjunction with tissue-type plasminogen activator and aspirin for acute myocardial infarction: results of the Thrombolysis in Myocardial Infarction (TIMI) 5 trial J Am Coll Cardiol, 1994;23:993-1003 CP Cannon et al.

Initial Experience with Hirudin and Streptokinase in Acute Myocardial Infarction: Results of the Thrombolysis in Myocardial Infarction (TIMI) 6 trial Am J Cardiol 1995;75:7-13 L. Veronica Lee.

* cited by examiner

HIRULOG-LIKE PEPTIDE AND GENE THERAPY

CROSS REFERENCE TO RELATED APPLICATIONS

This application is a continuation of U.S. Ser. No. 09/822,882, filed Mar. 30, 2001 now abandoned, which claims priority to U.S. Ser. No. 60/193,114, filed Mar. 30, 2000, both of which are incorporated herein by reference.

CROSS-REFERENCE TO RELATED APPLICATIONS

This application claim the benefit of priority under 35 U.S.C. § 119(e) of U.S. Provisional Application No. 60/193,114, filed Mar. 30, 2000, which is incorporated herein by reference.

BACKGROUND OF THE INVENTION

1. Field of the Invention

The present invention relates to the prevention of vascular restenosis either through drug therapy or by gene therapy.

2. Description of Related Art

Thrombin, the central enzyme of coagulation cascade, elicits a number of cellular responses relevant to haemostasis, fibrinolysis, cell growth, inflammation, wound healing and tissue remodeling. Thrombin-specific inhibitors, hirudin and hirulog-1, reduced ischemic events in coronary artery disease (CAD) patients.

Restenosis is one of the major concerns for the treatment of CAD using therapeutic vascular interventions. Classical anticoagulants did not effectively prevent restenosis but increased the frequency of bleeding complications. Thrombin inhibitors have been considered as potential candidate for the treatment of restenosis, although long-term benefit of the thrombin inhibitors on restenosis has not been shown in humans.

Recent studies in experimental animal models have demonstrated that the regimen for thrombin inhibitors is an important determinant of their therapeutic efficacy. The major limitation for using prolonged and large doses of thrombin inhibitors in patients is bleeding complications. At effective doses, hirulog-1 increased bleeding tendency in rats.

Thrombin, a key enzyme for haemostasis and several other important physiological processes, is a product of activated coagulation cascade. (Fenton, et al 1998). The generation of thrombin takes place on phospholipid-rich cell surfaces via a series of proteolytic reactions. Surface of activated platelets or injured vascular intima provides an optimal locus for coagulation reactions which stimulate the generation of thrombin from its precursor. Thrombin is involved at all levels of haemostasis, including plasma, blood cells and vasculature. Thrombin stimulates the formation of fibrin clot. It also activates several other coagulation factors (factor V, VIII and XIII) which further increase the generation of thrombin. Thrombin is a potent agonist for platelet secretion and aggregation. The secretory products of platelets enhance coagulation and thrombin formation. On the other hand, thrombin activates protein C by increasing its binding to thrombomodulin on endothelial cell (EC) surface (Esmon C T. 1983). Activated protein C inhibits coagulation by inactivating factor Va and VIIIa.

Besides its central role in hemostasis, thrombin stimulates the production of plasminogen activators (PA) and their major physiological inhibitor, plasminogen activator inhibitor-1 (PAI-1) in vascular EC and smooth muscle cells (SMC). Those fibrinolytic regulators modulate the generation of plasmin, a serine proteinase functions in dissolving fibrin clots and tissue remodeling (appendix IV). Thrombin induces the secretion of α-granule contents from platelets, including P-selectin (CD62P), an adhesion molecule involved in platelet aggregation, inflammation and thrombosis (Nguyen A, Gemmell et al, 1998). Thrombin is also a potent mitogen. It stimulates the expression of multiple growth factors in vascular cells, including platelet-derived growth factor (PDGF), basic fibroblast growth factor (bFGF), heparin binding epithelial growth factor (HBEGF) and transforming growth factor-β (TGF-β). Elevated expression of those growth factors has been detected in injured arterial walls (Ross R, et al 1986; Stouffer G A et al, 1998). Cellular responses of thrombin are usually mediated through the activation of its membrane receptor (Huang R. et al 1991).

The thrombin receptor has a long extracellular extension, which contains a proposed cleavage site for the enzyme and a binding site for thrombin. The proteolytic cleavage of thrombin receptor generates a short peptide with a newly exposed NH2 terminus, known as "tethered ligand", which helps to activate the receptor. The thrombin receptor has seven hydrophobic segments spanning the lipid bilayer of plasma membrane and its intracellular extension is coupled with G protein (Rasmussen U B et al 1991; Vu T K et al 1991).

Inhibitory G protein-coupled thrombin receptor, tyrosine kinase, phospholipase C and protein kinase C are involved in the regulation of thrombin-induced PAI-1 production in vascular SMC (Shen G X et al 1998; Ren S et al 1997). Thrombin may elicit multiple cellular responses related to cell growth and tissue remodeling via transmembrane signaling, which may be blocked by inhibitors targeted to the thrombin receptor or corresponding signaling pathway.

Vascular procedures, including angioplasty and endarterectomy, relieve atherosclerotic vascular stenosis without surgical intervention (Ryan T J et al 1988; Lincoff A M et al, 1993). However, angiographic or clinical restenosis occurred in 30%-50% of patients within 6 months after vascular procedures (Libby P et al, 1992; Clowes A W, Reidy M A, 1991). Histological studies demonstrated that SMC are the major cellular component in injury-induced neointima and restenotic lesions (Narins et al, 1998). Multiple biological processes are involved in the development of restenosis, including platelet activation, thrombus formation, SMC proliferation, tissue remodeling, EC activation, inflammation, oxidation and the expression of growth factors and oncogens (Scwartz S M et al, 1996). Proteases, including plasmin and metalloproteinases, may contribute to tissue remodeling and neointima formation following vascular injury (Libby P et al, 1992; Popma J J et al, 1993). The formation of plasmin is activated by tissue and urokinase plasminogen activators (tPA and uPA). Transgenic mice expressing uPA developed less extent of neointima induced by balloon injury (Carmeleit P, et al 1997). Increased levels of PAI-1 were found in plasma of patients developed angioplasty-induced restenosis (Ishiwata S et al 1997). The generation of uPA, tPA and PAI-1 from vascular cells is stimulated by thrombin. Increased levels of P-selectin, a marker for platelet aggregation responding to thrombin stimulation, were detected in plasma of patients with post-angioplasty restenosis (Ischinger T A, 1998; Ishiwata S et al, 1997, Tsakirirs D A et al, 1999). Stent implantation following angiography has virtually abolished periprocedural obstructive dissection and delays the occurrence of restenosis. The rates of intracoronary thrombosis and late restenosis were not reduced by stent implantation. Recurrent in-stent restenosis or vascular complications frequently occurred in the receivers. Stent-related vascular complications were found in some receivers. Extensive anticoagulant treatment is essential for post-stent management, which greatly increases the risk of bleeding (Safian R D et al, 1990; Carmeliet P et al 1997). Vascular restenosis remains as one of the major concerns for the treatment of atherosclerotic cardiovascular diseases using therapeutic vascular interventions.

Pharmacological prevention of vascular restenosis is highly demanded. Traditional anti-thrombotic agents, heparin, aspirin or oral anti-coagulants, did not effectively reduce the frequency of restenosis and increased bleeding complications (Buchanan M R et al, 1999). A variety of drugs has been tested in experimental animal vascular injury models and some of them were used in clinical trials (Lefkovitis J et al, 1997; Liu L Y et al, 1996). Several types of drugs appear to be potential, including PDGF antagonist (trapidil) (Maresta A, 1994), antioxidants (probucol, vitamin C and E) (Ferns G A et al 1992; Vermylen J, 1995) and thrombin-specific inhibitors (hirudin, hirulog-1) (Sarembock I J et al 1996; Gallo R et al 1998). The efficacy and safety of all those drugs for the prevention of restenosis in humans remains to be determined. Chimeric monoclonal antibody for glycoprotein IIB/IIIA receptor (abciximab or Reopro) improved the outcome of post-angioplasty CAD patients (Lefkovits J, 1996) but did not reduce intima hyperplasia or restenosis (Deitch J S et al, 1998; McGregor M et al, 1999).

Anti-thrombin III inhibits clotting factor by forming complexes with them. Heparin enhances the effect of anti-thrombin III by thousands-fold and it is the most commonly used anticoagulant in clinical practice (Hull R D, 1992). The major complication of heparin treatment is haemorrhage. Most of bleeding complications occurred at the puncture sites, but around 0.9% of heparin receivers developed intracranial haemorrhage (J Neurol Neurosurg Psychiatry 1996). In some individuals, heparin treatment caused thrombocytopenia and intravascular thrombosis. Heparin is not effective for thrombolysis, which probably is due to lack of access to thrombin in clots (Weitz J I et al, 1990). Besides, heparin suppressed the production of tPA but not PAI-1 in cultured SMC, which potentially attenuates fibrinolytic activity (Au Y P T et al, 1991). Low molecular weight (LMW) heparin caused less profound effect on haemorrhagic complications than regular heparin (Hirsh J et al., 1999). However, treatments with LMW heparin did not significantly reduce angiographic or clinical restenosis (Gimple L W et al, 1999).

Thrombolytic agents, including streptokinase, recombinant tPA, uPA and anisoylated plasminogen streptokinase activator complex, have been approved for the treatment of acute myocardial infarction. Those agents were also effective in relieving peripheral vascular thrombosis, pulmonary embolism and the restoration of the patency of catheter. Thrombolytic agents directly stimulate the formation of plasmin which functions in dissolving fibrin clots. The activity of tPA is greatly increased in the presence of fibrin (Garabedian H D et al, 1987). The major concern for using thrombolytic agents is high incidence of life-threatening bleeding complications and reocclusion. Intracranial haemorrhage, occurred in 0.5% of the receivers. Reocclusion of vessels following thrombolytic treatment was found in 10%-20% of receivers due to unidentified mechanism (Lavie C J et al 1990). Excess expression of uPA, promoted neointima formation in arteries following vascular injury in animal models (Carmeleit P et al, 1997). Those findings imply that thrombolytic agents and heparin may not be ideal candidates for preventing restenosis.

Hirudin is a 65 amino acid protein originally isolated from medicinal leech (Harvery R P et al 1986). It is the most potent natural thrombin-specific inhibitor. Results of the Helvetica trial showed that hirudin treatment reduced early cardiac events but had no long-term benefit for restenosis in post-angioplasty patients. In that study, hirudin was given in bolus injection plus intravenous infusion for 24 hours with and without subcutaneous booster injections. No description was provided from that report on the starting time of hirudin infusion relevant to angioplasty. Similar frequency of major bleeding (6%-7%) was found in hirudin receivers compared to conventional heparin treatment (Serruys R W, 1995). More recent studies indicated that modifications on the regimen of hirudin may considerably improve its anti-restenosis effect in animals. Prolonged infusion of hirudin for two weeks effectively reduced angioplasty-induced stenosis in swine model compared to bolus or short infusion (Gallo, R, et al, 1998). Infusion of hirudin for 24 hours started before angioplasty significantly reduced angioplasty-induced restenosis in atherosclerotic rabbits compared to four hours or delayed infusion of hirudin (Thome L M et al, 1998). Intravascular gene transfer of hirudin reduced balloon catheter injury-induced neointima formation by 50% in rats (Rade, J J, et al, 1996). Those findings suggest that the earlier results from clinical trials on the ineffectiveness of hirudin on restenosis may need to be re-evaluated using rationalized regimen. Results from phase II clinical trials suggested that hirudin reduced ischemic events in angina, post-myocardial infarction or post-angioplasty patients without significant increase in bleeding complications compared to conventional heparin treatment (Van den Bos, et al, 1993; Topol E J, et al, 1994; Cannon, C P, et al 1994; Lee, L V, 1995). Phase III clinical trials in large scales of patients indicated that hirudin caused high incidence of life-threatening haemorrhage (Adgey, A A, 1996). One of the trials found that the incidence of major bleeding complications at non-cranial sites in hirudin-treated patients (7%) was over two-fold higher than conventional heparin treatment (3%), and the trial was prematurely suspended (Antman, E M, 1996). Two other trials were stopped after the enrollment of 302 and 2,564 patients due to high incidence of intracranial haemorrhage in hirudin-treated patients compared to conventional heparin treatment (GUSTO, 1994; Neuhaus, K L, et al, 1994). High frequencies of life-threaten bleeding complications limit the application of hirudin in stable CAD patient.

Hirulogs are a group of synthetic thrombin-specific inhibitors which conserve the major active sites of hirudin. Hirulog-1, a 20-residue peptide, is the strongest hirulog (Maraganore, J M, 1990; Ofosu, F A, 1992). It is composed of a N-terminal domain (D-FPRP), which blocks the enzymatic active site, and a C-terminal domain (NGDFEEIPEYL SEQ. ID NO:3) inhibiting the binding of thrombin to its receptor. Hirulog-1 treatment effectively prevented acute cardiovascular events in post-myocardial infarction (Lidon, R M, 1993), coronary angiography (Lidon, R M, 1994) and percutenous transluminal coronary angioplasty (PTCA). (Bittl, J A, 1995). Since hirulog-1 is a peptide in nature and is quickly metabolized in gastrointestinal tract via oral intake, it has only been administrated via intravenous route as other peptide drugs. The plasma half-life of hirulog-1 in human is 15-20 minutes (Fenton, J W, 1992). Allergy to hirulog-1 has not been reported probably due to the weak antigenicity of the peptide. Phase III clinical trials demonstrated that hirulog-1 increased bleeding complications in CAD patients following angioplasty, but the incidence was lower than conventional heparin treatment (Bittl, J A, 1995). Continuous intravenous infusion of hirulog-1 reduced platelet deposition 30 minutes after endarterectomy with and without aspirin administration (Hamelink, J K, 1995; Jackson, M R et al, 1996). Hirulog-1 inhibits thrombin-induced production of PAI-1 in cultured arterial SMC (appendix III). In diet-induced atherosclerotic rabbits, hirulog-1 infusion reduced restenosis induced by angioplasty compared to heparin treatment (Sarembock, I J, et al, 1996). Hirulog-1-impregnated silicone polymers placed around adventitia surface of stented segments did not inhibit stent-induced stenosis in pig carotid artery. The results of that study was questioned by the uncertainty of the delivery of hirulog-1 to vascular lumen (Muller, D W, 1996). The applicant's group demonstrated that hirulog-1 inhibited platelet deposition on intima denuded by balloon catheter in rats (Shen, G, et al, 1997). Multiple prolonged infusions of hirulog-1 (1 mg/kg/hours for 4 hours for 6 times, immediately following injury and every other days after for 5-times) inhibited balloon catheter injury-induced increase in neointima/media ratio by 50% in rat carotid arteries. Some results demonstrated that hirulog-1 infusions attenuated the abundance of PDGF in neointima of rat carotid arteries. Tail bleeding time and aPTT were significantly elongated by hirulog-1 treatment in rats. Those results indicated that hirulog-1 effectively reduces balloon catheter injury-induced neointima formation in rats. The preventive effect of hirulog-1 on neointima formation may result, at least partially, from its inhibition on PDGF expression in vascular wall. Impaired coagulation activity and prolonged bleeding time were detected in hirulog-1-treated rats, which potentially cause haemorrhage when large doses of the inhibitor are administrated.

As discussed, Hirulog-1, a synthetic thrombin inhibitor, is effective in preventing ischemic events in coronary artery disease and causes significantly less bleeding complications than classical anticoagulants. Studies have demonstrated that hirulog-1 inhibited thrombin-induced PAI-1 production in SMC (Ren et al J Vas Res 1997;29:337-42). Hirulog-1 inhibited thrombin-induced SMC proliferation (Ren et al unpublished observations). Bolus injection of hirulog-1 transiently reduced platelet deposition on intima following balloon catheter injury in rats. Multiple prolonged intravenous infusions of hirulog-1 partially prevented balloon injury-induced neointima formation.

Clinical studies demonstrate that hirulog-1 treatment was equal or more effective on preventing ischemic events in coronary artery disease and caused significantly less major bleeding complications than classical anticoagulants. Recent studies demonstrated that hirulog-1 inhibited the production of plasminogen activator inhibitor-1 and thymidine incorporation in cultured smooth muscle cells (SMC). In addition, hirulog-1 injection inhibited balloon injury-induced platelet deposition, thrombin activation and reduced neointima formation in carotid arteries in rats. Hirulog-1 contains unnatural amino acid which prevents this peptide from being expressed in mammalian cells.

Vascular restenosis induced by angioplasty and other vascular intervention is a major concern for the treatment for coronary heart disease. Ischemic events occur within in months of 40% patients receiving angioplasty. No effective treatment is available for vascular restenosis. It would therefore be useful to develop a treatment of vascular restenosis without any of the drawbacks set forth above.

SUMMARY OF THE INVENTION

According to the present invention, there is provided a hirulog-like peptide. Also provided is the treatment of vascular restenosis including the step of administering an effective amount of a hirulog-like peptide in a pharmaceutically acceptable carrier whereby administration prevents vascular restenosis. A pharmaceutical composition including a hirulog-like peptide and a pharmaceutically acceptable carrier is also provided. A vector expressing a hirulog-like peptide is also provided. The present invention also provides a method of treating a patient with vascular restenosis including the step of introducing to the patient an amount of a sequence encoding a hirulog-like peptide sufficient to prevent vascular restenosis.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
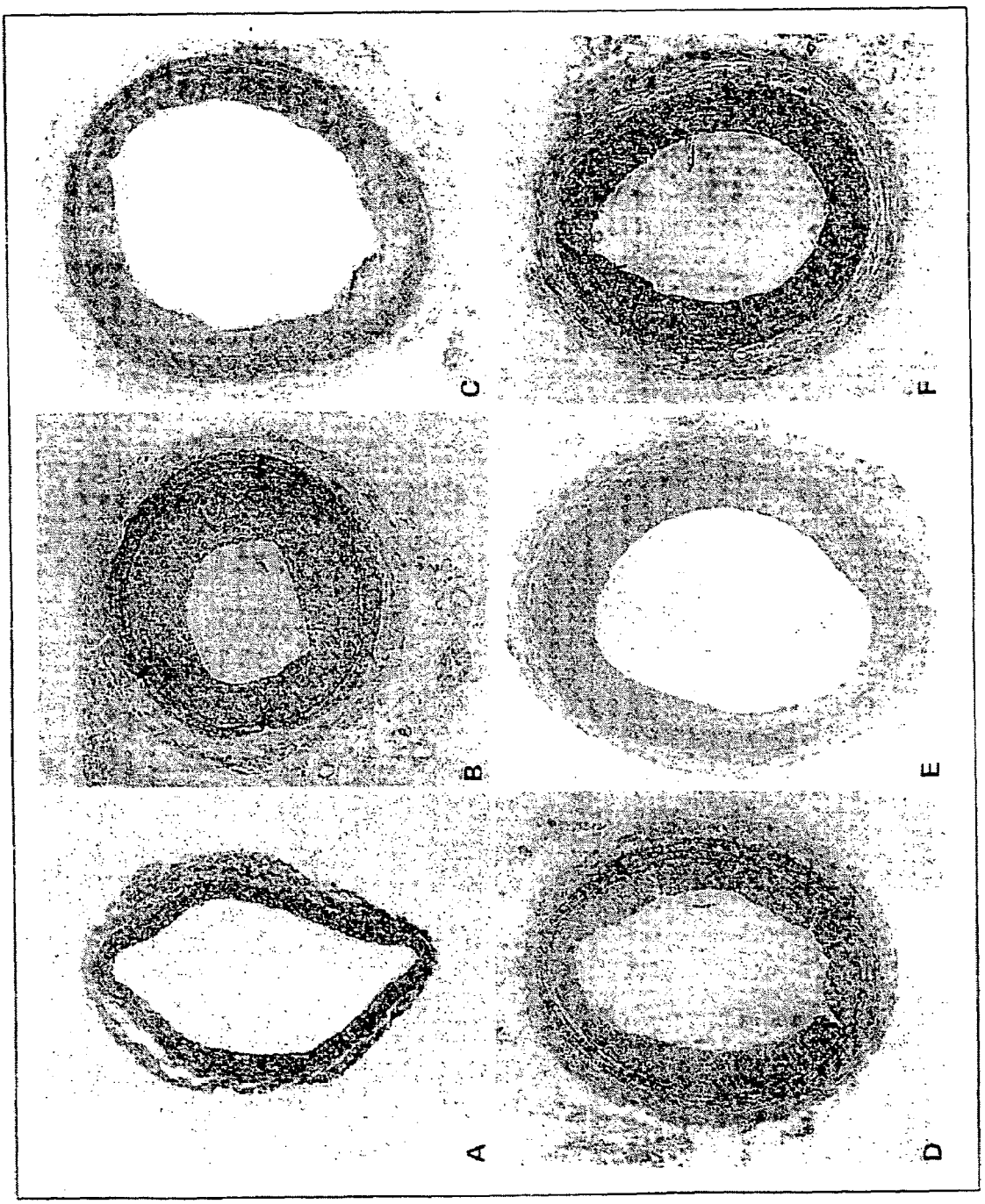
FIGS. 1 A-F show the effects of the hirulog-like peptide on balloon catheter injury-induced neointima formation in rat carotid arteries.

Generally, the present invention provides a hirulog-like peptide. The peptide prevents vascular restenosis without the detriment side effects found from treatment with hirulog-1. The hirulog-like peptide is synthesized using procedures known to those of skill in the art, and can include homologues of the sequence.

Gene therapy of hirulog improves the effect of intravenous administration of hirulog-1 on injury-induced stenosis. To achieve this goal, a biological effective hirulog-like peptide (HLP) without unnatural amino acids was identified. The present invention provides a HLP (32 amino acids) based on the structures of hirulog-1 and thrombin receptor (FPESKAT-NATLDPRPGGGGNGDFEEIPEEYLQ) (SEQ ID No:1). Multiple prolonged intravenous infusions of HLP inhibited balloon catheter injury-induced stenosis by 30%-40%. Unlike hirulog-1, HLP at the effective doses for the prevention of neointima information did not significantly alter coagulation activity. The Ki of HLP is two orders of magnitude higher than hirulog-1 on the thrombin inhibition. It is a potential drug to reduce vascular restenosis in coronary heart disease induced by vascular procedures without the risk of hemorrhage.

HLP is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art. The amount must be effective to achieve improvement including but not limited to improved survival rate, more rapid recovery, or improvement or elimination of symptoms.

A pharmacological formulation of HLP can be administered to the patient in an injectable formulation containing any compatible carrier, such as various vehicle, adjuvants, additives, and diluents; or the compounds utilized in the present invention can be administered parenterally to the patient in the form of slow-release subcutaneous implants of the HLP, or iontophoretic, polymer matrices, liposomes, and microspheres can be employed. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

HLP is composed of all natural amino acids and it is able to be expressed in a mammal through gene therapy. The present invention provides for gene therapy of HLP to deliver and improve the effect of this drug on the prevention of vascular restenosis. The method of the present invention can be applied to the management of metastases and thrombotic complications.

Intravascular transfer of vector-mediated HLP gene provide an alternative therapy against both restenosis and thrombosis with following advantages: i) inducing secretion of a thrombin-specific inhibitor without non-specific effects; ii) HLP causes lower frequency of bleeding complications than heparin or hirudin; iii) the location for the expression of HLP can be highly selective, which helps to prevent thrombosis and vascular stenosis at specific site; iv) avoid multiple injections or intravenous infusion; v) the expression of HLP is engineered to spontaneously cease 2-3 weeks after the infection, but it may be ideal for preventing restenosis with an anticoagulant; vi) no risk of malignancy in humans. In an embodiment the vector is adenoviral as described herein below.

In further embodiments the gene therapy method and vector of the present invention include: i) prevent restenosis following vascular procedures, such as angioplasty, intravascular metallic stent, endarterectomy and coronary artery bypass; ii) prevent occlusive vascular diseases in patients with known high risk of thrombosis or vascular stenosis, such as diabetes and atherosclerosis; iii) a supplemental treatment for patients with solid and haematological malignancies to prevent hyperthrombinemia-related metastasis and thrombotic complications.

By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. Alternatively, the genetic material of interest encodes a suicide gene. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ [Culver, 1998]. These genetically altered cells have been shown to express the transfected genetic material in situ.

The gene expression vehicle is capable of delivery/transfer of heterologous nucleic acid into a host cell. The expression vehicle can include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore as used herein the expression vehicle can, as needed, not include the 5'UTR and/or 3'UTR of the actural gene to be transferred and only include the specific amino acid coding region.

The expression vehicle can include a promotor for controlling transcription of the heterologous material and can be either a constitutive or inducible promotor to allow selective transcription. Enhancers that can be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation does not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention depends on desired cell type to be targeted and is known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed do not contain a genome and therefore cannot proceed through subsequent rounds of infection. The specific type of vector depends upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting, vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

In an embodiment, the structure of recombinant HLP DNA cassette contains: i) human growth hormone (hGH) signal sequence for facilitating secretion [Rade J J et al. 1996 Nature-Med 2:293-8]; ii) HLP DNA which is composed of DNA sequence encoding a 12 amino acid leading sequence, hirulog-2-9 [Maraganore J M et al. 1990 Biochemistry 29:7095-101] and hirudin54-65 [Forckamp E et al. 1986 DNA 5:511-7]. Antisense single-strand DNA encoding the prototype of HLP and sense single-strand DNA encoding hGH signal peptide is synthesized. Double-strand HLP-hGH DNA is generated from the synthesized DNA templates by two-step PCR with the help of two terminal primers [Rade J J et al. 1996 Nature-Med 2:293-8]. Design of PCR primers utilized DNAStar software. Recombinant HLP DNA is cloned into pBluescript IISK+ (pHLP) for amplification. The sequence of HLP-hGH DNA is verified by DNA sequencing using-dideoxy method.

The embodiment further provides for the preparation of shuttle plasmid containing HLP gene. HLP cDNA is cloned into pAdvBgl II adenoviral plasmid (Bgl II site) to generate AdHLP in the Co-applicant's laboratory. The structure of the recombinant plasmid is confirmed by DNA sequencing. Functionality of AdHLP is confirmed in vitro by transfecting human EC and SMC, and analysing secreted HLP from the media.

The embodiment further includes construction of adenoviral vector in 293 embryonic kidney cells. E1-E3-deleted adenoviral vectors (serotype 5) [Ghosh-Choudhury G et al. 1986 Gene 50:161-71] containing HLP cDNA are constructed. Generally expression of HLP is driven by the powerful human cytomegalovirus (CMV) promoter but other expression cassettes as known in the art can be used. Replication-deficient adenoviruses are produced in 293 cells and concentrated by ultracentrifugation. Adenoviral preparations are analyzed for the absence of helper viruses, microbiological contaminants and lipopolysaccharides. AdLacZ is used as a control.

The embodiment provides for verification of the expression of HLP. The expression of $\alpha$-galactosidase in 293 cells is verified by staining as previously described [Yla-Herttuala S et al. 1995 J Clin Invest 95:2692-8]. The infection of HLP in 293 cells is examined by Southern and Northern blotting analyses using radioactively labeled HLP DNA as probe. The activity of HLP in the media is determine by measuring QTT as previously described [Reid T J, Alving B M. 1993 Thromb Haemost 70:608-16]. Monoclonal antibody against synthesized HLP is raised and an ELISA for HLP is developed as previously described [Klewis L et al. 1993 Biochem J 290: 791-5] for measuring HLP mass.

As shown in Example 1, the effects of hirulog-1 on neointima formation, platelet deposition, coagulation activity, and platelet-derived growth factor (PDGF) in balloon catheter injured carotid artery in Sprague-Dawley rats were determined. Multiple intravenous infusions of hirulog-1 (1 mg/kg/hours for 4 hours×6-times) reduced neointima/media ratio by 50.8% in carotid arteries injured by balloon catheter compared to animals injured by the same way but without treatment. Bolus injection of hirulog-1 transiently elongated activated partial thromboplastin time in arterial blood circulation and inhibited platelet deposition on denuded intima visualized under scanning electron microscopy. Hirulog-1 treatment attenuated the abundance of PDGF in the neointimal layer of catheter injured arterial wall detected by immunohistochemistry.

The results indicate that hirulog-1 treatment substantially reduced catheter injury-induced neointima formation in rats. The inhibition on platelet deposition and PDGF expression may contribute to the beneficial effect of hirulog-1 on injury induced vascular stenosis. Hirulog-1 may be considered as an alternative for the prevention of restenosis induced by vascular interventions. A further detailed description of the use of the hirulog-like peptide itself is set forth in Examples included herewith and incorporated by reference in their entirety.

The above discussion provides a factual basis for the use of HLP. The methods used with and the utility of the present invention can be shown by the following non-limiting examples and accompanying figures.

EXAMPLES

General Methods:

General methods in molecular biology: Standard molecular biology techniques known in the art and not specifically described are generally followed as in Sambrook et al., Molecular Cloning: A Laboratory Manual, Cold Springs Harbor Laboratory, New York (1989, 1992), and in Ausubel et al., Current Protocols in Molecular Biology, John Wiley and Sons, Baltimore, Md. (1989). Polymerase chain reaction (PCR) is carried out generally as in PCR Protocols: A Guide To Methods And Applications, Academic Press, San Diego, Calif. (1990). Reactions and manipulations involving other nucleic acid techniques, unless stated otherwise, are performed as generally described in Sambrook et al., 1989, Molecular Cloning: A Laboratory Manual, Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays: In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, Molecular Cloning: A Laboratory Manual, Cold Springs Harbor, N.Y., 1989

Antibody Production: Antibodies can be either monoclonal, polyclonal or recombinant. Conveniently, the antibodies can be prepared against the immunogen or portion thereof for example a synthetic peptide based on the sequence, or prepared recombinantly by cloning techniques or the natural gene product and/or portions thereof can be isolated and used as the immunogen. Immunogens can be used to produce antibodies by standard antibody production technology well known to those skilled in the art as described generally in Harlow and Lane, Antibodies: A Laboratory, Manual, Cold Spring Harbor Laboratory, Cold Spring Harbor, N.Y., 1988 and Borrebaeck, Antibody Engineering—A Practical Guide, W.H. Freeman and Co., 1992. Antibody fragments can also be prepared from the antibodies and include Fab, F(ab')2, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 4995), messenger RNAs from antibody producing B-lymphocytes of animals, or hybridoma are reverse-transcribed to obtain complimentary DNAs (CDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, Immunochemistry in Practice, Blackwell Scientific Publications, Oxford, 1982.) The binding of antibodies to a solid support substrate is also well known in the art. (see for a general-discussion Harlow & Lane Antibodies: A Laboratory Manual, Cold Spring Harbor Laboratory Publications, New York, 1988 and Borrebaeck, Antibody Engineering—A Practical Guide, W.H. Freeman and Co., 1992) The detectable moieties contemplated with the present invention can include, but are not limited to, fluorescent, metallic, enzymatic and radioactive markers such as biotin, gold, ferritin, alkaline phosphatase, α-galactosidase, peroxidase, urease, fluorescein, rhodamine, tritium, 14C and iodination.

Recombinant Protein Purification: Marshak et al, "Strategies for Protein Purification and Characterization. A laboratory course manual." CSHL Press, 1996.

Delivery of Gene Products/Therapeutics (Compound):

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patent being treated and will vary from about 100 ng/kg of body weight to 100 mg/kg of body weight per day and preferably will be from 10 mg/kg to 10 mg/kg per day.

Example 1

Hirulog-1 Reduces Balloon Catheter Injury-Induced Neointima Formation, Platelet Deposition and Platelet-Derived Growth Factor in Rat Carotid Arterial Wall Vascular stenosis remains as the major concern for the treatment of atherosclerotic cardiovascular diseases using vascular interventions. Hirulog-1, a synthetic thrombin inhibitor, effectively reduced ischemic events in coronary heart disease patients and caused less haemorrhagic complications compared to classical anticoagulants. The effect of hirulog-1 on injured-induced vascular stenosis remains uncertain.

Thrombin is the product of prothrombin generated from the chain reaction of coagulation. The surfaces of activated platelets and injured vascular intima provide optimal locus for several critical coagulation reactions, which accelerates thrombin generation and platelet aggregation. Thrombin is involved at all levels of haemostasis (Fenton, II, J W 1998) and interferes with fibrinolysis through the regulation of the generation of plasminogen activators and their inhibitors from vascular cells (Esmon C T, 1983). Thrombin is also a potent agonist for the production of platelet-derived growth factor (PDGF) which promotes the proliferation of smooth muscle cells (SMC) (Nguyen A, 1998).

Hirudin, the most potent thrombin inhibitor, was originally isolated from medicinal leech, *Hirudo medicinalis*. Hirudin is one of the stronger anticoagulants and reduced vascular stenosis in experimental animal models (Ross, R, 1986; Stouffer, G A, et al 1998). However, the results from large scale clinical trials demonstrated that hirudin treatment induced significantly higher incidence of cranial or other major bleeding complications compared to heparin treatment (Huang R, 1991; Vu, T K, 1991). Hirulogs are a group of synthetic thrombin-specific inhibitors which were designed according to the sequences of hirudin. Hirulog-1 (bivalirudin, BG8967) is one of the most potent hirulogs. It is a 20-amino acid peptide (D-FPRPGGGGNGDFEEIPEEYL) (SEQ ID No:2) consisting of two moieties, one binds to the active site cleft of thrombin and the other is recognized by the anion-binding exosite of the enzyme (Shen, G X, 199-8). Hirulog-1 treatment effectively prevented acute cardiovascular events in post-myocardial infarction (Ren, S. et al, 1997) and vascular interventions (Ryan T J, et al, 1988; Lincoff A M, 1993). Different from hirudin, hirulog-1 caused significantly less bleeding complications compared to heparin (Lincoff A M, 1993).

Vascular restenosis occurs within months in 30-50% of patients receiving vascular interventions (Libby, P, et al, 1992; Clowes A W, et al, 1991). No effective therapy is currently available for preventing vascular restenosis. Previous studies demonstrated that hirulog-1 reduced platelet deposition on intima following endarterectomy (Narins C R, et al, 1998). The impact of hirulog-1 on experimental injury-induced vascular stenosis remains controversial (Popma J J et al, 1993; Carmeleit P et al, 1997). The present experiment examined the effect of hirulog-1 administration on balloon catheter injury-induced stenosis in rat carotid artery. The influence of hirulog-1 on platelet deposition on endothelium denuded intima, coagulation activity and the abundance of PDGF in arterial wall was further investigated.

Methods

Vascular injury animal model: Male Sprague-Dawley rats (380-420 g) on regular chow were anaesthetized by intraperitoneal injection with ketamine (0.24 mg/kg) and xylazine (0.15 mg/kg). Right external carotid artery was ligated at the level of mandible by silk. Internal and proximal common carotid arteries were temporarily clamped. An incision was made on proximal external carotid artery. Arterial embolectomy catheter (size 2F, Baxter, Irvine, Calif.) was inserted through the incision into common carotid artery. Endothelial denudation was achieved by mechanically pulling catheter for 5-times in the lumen of common carotid artery when the balloon of catheter was intermittently inflated with 3 pound/inch2 of pressure monitored using a 20/20 indeflator (Ishiwata S et al, 1997).

Pharmacological treatment: Hirulog-1 was customerly synthesized according to previously reported sequence (9) in Manitoba Institute of Cell biology, Winnipeg, Manitoba. Synthesized hirulog-1 purified by high performance liquid chromatography was dissolved in saline. Bolus injection was administrated via carotid artery or penile vein. Intravenous infusion were administrated via femoral vein through a polystaltic pump for indicated periods. Control animals received equal volume of saline via matching routs.

Histological analysis: At the end of experiments, right common carotid arteries were isolated. Vascular tissue was immersed in 4% formaldehyde and subjected to paraffin embedding. Sections in 5 μm thickness were mounted on glass slides and stained with haematoxylin and eosin. Continuous cross-sections were observed under light microscopy to identify maximal vascular stenosis for subsequent analysis. Residual lumen was designated as lumen formed after injury. Media area was calculated from the area between external and internal elastic lamina. The extent of neointimal thickening was expressed as follows: neointimal area, the area between internal elastic lamina and residual lumen; stenosis, the percentage of neointimal area/area of residual lumen+neointimal area; neointima/media (N/M), the ratio of neointimal area/media area (Ischinger T A, 1998).

Scanning electron microscopy (SEM): Arterial segments were immersed in 0.1 M phosphate buffer containing 4% glutaraldehyde (pH 7.4) for 24 hours then fixed in 1% osmium tetroxide for 1 hours at 25° C. Vascular specimens were dehydrated with increasing concentrations of ethanol and dried under carbon dioxide. Lumenal surfaces of arteries were coated with a layer of fine-coat palladium (150-200 Å, Hummer V, Technics) and examined under SEM (JEOL 35, Japan). Platelets on intima were counted on SEM image (×1,000). Each value of platelet counting was generated from the average of 4 readings from different fields (2,500 μm$^2$/field).

Immunohistochemistry: Sections of vessels tissue embedded in paraffin were dewaxed by decreasing concentrations of ethanol followed by treatment with 10% hydroxyperoxide then with 0.05% trypsin. After rinsing with phosphate buffered saline, sections were incubated with one of the following types of primary antibody, polyclonal antibodies against human PDGF (Calbiochem, Cambridge, Mass.), monoclonal antibody against SMC$_\alpha$-actin (Sigma, St. Louis, Mo.) or non-specific rabbit serum IgG, at 4° C. for overnight. Subsequently, sections were treated with appropriate biotinylated second antibodies for 30 minutes at room temperature then with streptavidin peroxidase. The bindings of antibodies were visualized by Histomark Orange system (Kirkegaard and Perry Laboratories, Gaithersburg, Md.) (Ishiwata S et al, 1997). For nucleus counter-stain, immunostained sections were incubated with haematoxylin solution for 30 minutes then washed with ethanol and HCl. After dehydration with isopropyl alcohol and xylol, the sections were examined under light microscopy.

Quantitative thrombin time (QTT) and activated partial thromboplastin time (aPTT): Plasma levels of hirulog-1 were estimated using QTT as previously described (Safian R D et al, 1990). Synthesized hirulog-1 (>90% of purity) was used as standard. The levels of aPTT in plasma were analyzed using a MLA 1000C Coagamate XM system in Haematology Laboratory, Health Sciences Centre, Winnipeg.

Statistics: Student's t-test was used for the comparisons of probabilities between two groups. One way ANOVA analysis plus Duncan's test were performed for the comparisons between multiple groups. The level of significance was defined as $p<0.05$. Correlation analysis was performed using Sigmaplot Window version software.

Results

Histological changes in balloon catheter injury-induced vascular stenosis: The thickness of intima of intact artery was negligible at the magnitude of ×40 (FIG. 1A). Neointima in carotid artery was not evident at 3 days after balloon catheter injury. The thickness of neointima was moderately increased at 1 week following the injury (data not shown). At 2 weeks following injury, a thick layer of neointima was formed and that was associated with an apparently narrowed lumen (FIG. 1B). The levels of neointima/media, (N/M), stenosis and neointima area in catheter injured carotid arteries were 1.28±0.03, 51.4±1.36(%) and 182.9±54.0×1000 μm2/section (mean±SE, n=9), respectively. In 3 other rats, the lumens of carotid arteries were completely occluded by thrombi at 2 weeks after the injury.

Effect of hirulog-1 on injury-induced vascular stenosis: Bolus injection of 1 mg/kg of hirulog-1 through venous or arterial route immediately after catheter injury did not affect neointima formation at 2 weeks after injury. No significant reduction of neointimal thickness was detected following intravenous infusion of hirulog-1 (1 mg/kg/hours) for 4 hours (immediately after the injury, FIG. 1C). In animals received intravenous infusions of hirulog-1 at the same dose for 4 hours×6-times (immediately after injury and following every other days for 5-times), the thickness of neointima was obviously reduced (FIG. 1D) compared to that in injured animals without treatment (FIG. 1B). This was associated with larger lumens and more flexible vascular walls compared to injured animals without treatment (FIG. 1B). The levels of N/M, stenosis and neointimal area in injured rats infused with hirulog-1 for 6-times were 50.8±3.3%, 37.0±2.6% and 56.3±3.8% (mean±SE) lower than those in catheter injured animals without treatment ($p<0.001$). No significant change in those parameters was found in rats receiving once or twice infusions of hirulog-1 (FIG. 2).

Effect of hirulog-1 on platelet deposition: Platelet deposition on intima was estimated using SEM. On the intima of carotid arteries without injury, endothelium was recognized by elevated nuclei of endothelial cells (bright spindle-like spots in FIG. 3A). No platelet was deposited on intact endothelium of carotid arteries. At 15 minutes after balloon catheter injury, numerous platelets were detected on denuded intima (FIG. 3B). Multiple layers of platelets were detected on intima at 30 or 60 minutes after the injury. Those images were not used for platelets counting, since the number of platelets may be underestimated due to inaccurate counting of overlapped platelets. Bolus injection of hirulog-1 (1 mg/kg) via both carotid artery (FIG. 3C) and penile vein (FIG. 3D) effectively inhibited the deposition of platelets on injured intima at 15 minutes after the injury.

Figure 4:
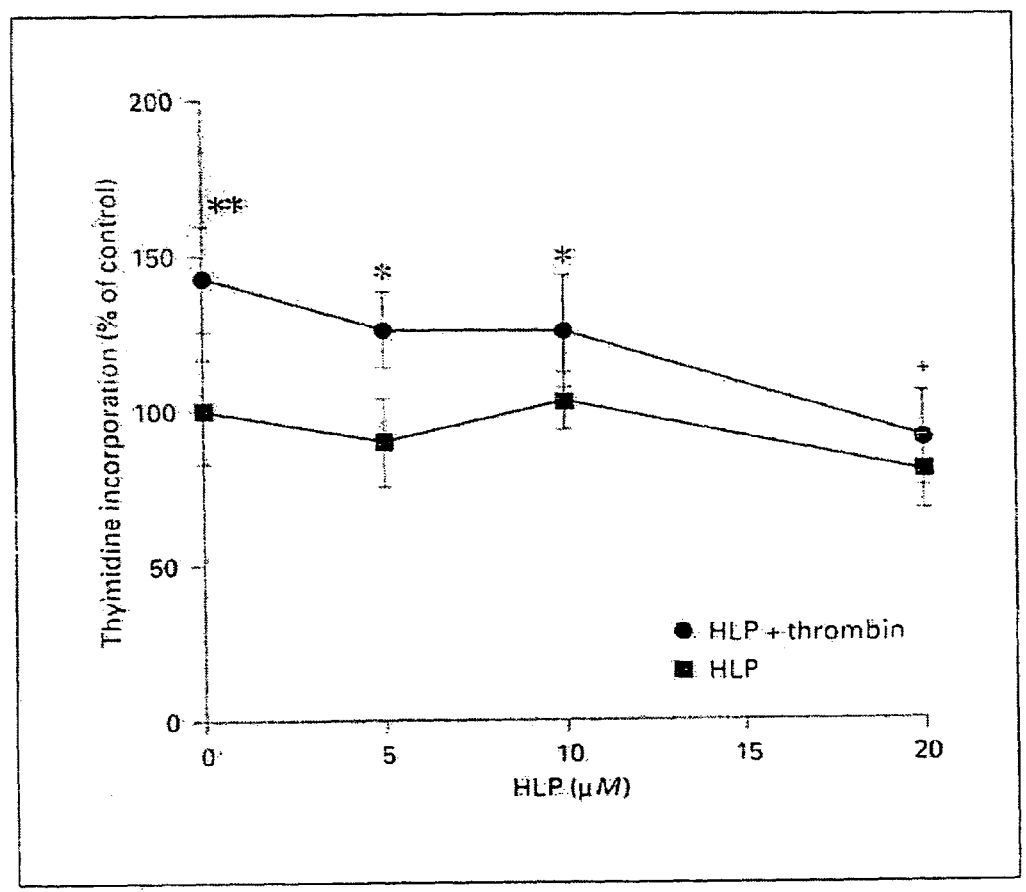
FIG. 4 shows the effects of HLP and thrombin-induced 3H-thymidine incorporation in baboon aortic SMC.

The inhibitory effect of hirulog-1 on platelet deposition was dose-dependent. Significant inhibition on platelet deposition was found in rats treated with 0.5 mg/kg of hirulog-1 for 15 minutes ($p<0.05$). The effects of hirulog-1 on platelet deposition reached a plateau beyond 1 mg/kg of hirulog-1 (FIG. 4). Significant reduction of platelet deposition was found at 5 minutes after the injection of hirulog-1 compared to untreated controls ($p<0.01$). The maximal inhibition of platelet deposition was achieved at 15 minutes after the injection and the effect was attenuated at 30 minutes following the treatment. No inhibition was found at 60 minutes after the injection compared to controls (FIG. 5). The levels of hirulog-1 in blood drawn from injured carotid arteries were estimated by measuring QTT. Arterial blood levels of hirulog-1 positively correlated with the amounts of platelets deposited on intima ($p<0.01$, FIG. 6).

Effect of hirulog-1 treatment on aPTT: The activities of coagulation in arterial blood of intact and catheter injured rats were monitored by measuring aPTT before and after hirulog-1 treatment. At 1 minute after injection of 1 mg/kg of hirulog-1, the levels of aPTT were raised 3- to 4-fold higher than basal levels in both uninjured and balloon catheter injured rats. Increases in aPTT in both groups were gradually reduced after single administration of hirulog-1 but remained to the levels higher than corresponding basal levels within 15 minutes after the injection ($p<0.05$). The levels of aPTT were normalized beyond 30 minutes following the treatment (FIG. 7).

Influence of hirulog-1 treatment on PDGF in neointima: The abundance of PDGF in vascular wall of carotid artery with and without balloon catheter injury was detected by immunohistochemistry using antibodies against PDGF. In arterial walls without balloon catheter injury, the binding of antibodies against PDGF to media was negligible (FIG. 8B). In comparison, α-actin was detectable in media of arterial wall without injury (FIG. 8C). Catheter injury resulted in strong immunostaining of PDGF and α-actin in neointima (FIGS. 8E and F). Hirulog-1 treatment (1 mg/kg/hours for 4 hours×6) obviously reduced the abundance of PDGF in neointima but did not apparently change the abundance of α-actin (FIGS. 8H and I). Comparable results were obtained from three independent experiments.

DISCUSSION: Vascular interventions including angioplasty, endarterectomy, and stent implant can dilate arteriosclerosis-induced vascular stenosis with minimal surgical interventions (Carmeliet P, et al, 1997; Buchanan M R et al, 1999). However, restenosis or ischemic events recurred in 30-50% of patients receiving vascular interventions within months (Libby P, et al, 1992; Clowes A W et al, 1991). Histological studies demonstrated that SMC are the major cellular component in neointima (Lefkovits J, et al, 1997). Since there is no effective management available, vascular restenosis becomes a major concern for the treatment of atherosclerotic cardiovascular diseases using vascular interventions.

Transfer of a number of genes intervening cell proliferation, coagulation or oxidation prevented or reduced vascular stenosis in animal models. (Liu L Y et al, 1996). Gene transfer of recombinant hirudin via adenoviral vector to rat carotid arterial wall reduced balloon injury-induced neointima formation by 35% (Ross R, et al, 1986). Intravenous infusions of high dose of hirudin (2 mg/kg/hours) inhibited balloon catheter-induced neointima formations (Stouffer G A, et al 1998). However, increased incidence of bleeding complications induced by high doses of hirudin raises concern. Earlier results from relatively smaller phase II trials (<246 patients/study) suggested that hirudin reduced the incidence of ischemic events in angina, post-myocardial infarction or post-angioplasty patients and did not significantly increase the incidence of bleeding complications compared to heparin (Maresta A, et al, 1994; Ferns G A; 1992, Vermylen J, 1995; Sarembock I J, 1996). Several larger scale phase III trials demonstrated that high doses of hirudin caused excess bleeding complications, which forced three studies to be prematurely ceased (Gallo R, 1998). One of the trials, suspended after randomization of 757 patients, revealed that the frequency of major bleeding complications at non-cranial sites in patients treated with hirudin (0.1 mg/kg of bolus plus 0.1 mg/kg/hours of infusion) was more than 2-fold higher than conventional heparin treatment (Huang R, et al, 1991). Two others trials, which were stopped after enrollment of 302 and 2,564 patients, demonstrated that hirudin treatment (0.4-0.6 mg/kg of bolus plus 0.15-0.2 mg/kg/hours of infusion) substantially increased the incidence of intracranial haemorrhage (1.3 and 3.4%) compared to heparin (0.6 and 0%) (Rasmussen U B et al, 1991; Vu T K et al, 1991).

The results of phase III clinical trails for hirulog-1 indicated this synthesized thrombin inhibitor reduced ischemic events and caused significantly less bleeding complications compared to conventional heparin treatment in unstable angina or post-myocardial infarction patients following angioplasty (Lincoff A M et al, 1993). In diet-induced atherosclerotic rabbits, hirulog-1 infusion reduced arterial restenosis after balloon angioplasty compared to heparin treatment. The extent of neointima formation in injured animals on high cholesterol diet but without treatment was not described in that study (Narins C R et al, 1998). Hirulog-1-impregnated silicone polymers placed at adventitia surface of stented segments failed to reduce stent-induced stenosis in porcine carotid artery. The conclusion of that study is questioned by the uncertainty of the delivery of hirulog-1 into vascular lumen (Scwartz S M et al, 1996). The present study demonstrates that multiple intravenous infusions of hirulog-1 substantially reduced catheter injury-induced neointima formation in rats. This suggests that hirulog-1 potentially reduces injury-induced vascular restenosis in the absence of hyperlipidaemia and atherosclerosis. In addition, hirulog-1 treatment inhibited balloon injury-induced platelet deposition on denuded intima and reduced the expression of PDGF in neointima, which potentially contribute to the beneficial effect of hirulog-1 on injury-induced vascular stenosis.

Both platelet adhesion and aggregation are involved in the deposition of platelets. Endothelial denudation and the exposure of collagen to blood components stimulate platelet deposition and thrombin formation (Nguyen A, et al, 1998). Previous studies found that intravenous infusions of hirulog-1 with or without aspirin reduced platelet deposition at 30 minutes after carotid artery endarterectomy (Libby P, et al, 1992; Clowes A W, et al, 1991). The results of the present experiment demonstrate that bolus injection of hirulog-1 inhibited platelet deposition on denuded intima occurring much earlier than previously described (Libby P, et al, 1992; Clowes A W, et al, 1991). Significant inhibition on platelet deposition was found as early as 5 minutes following the injection of hirulog-1. The inhibitory effect of hirulog-1 on platelet deposition reached a peak at 15 minutes after the injection. Intravenous infusions of hirulog-1 can steadily reduce platelet deposition on injured intima, which can decrease the release of numerous biological activators from platelets, including serotonin, ADP, and PDGF.

The expression of PDGF has been detected in platelets, SMC, endothelial cells, monocytes, embryonic cells, and megakaryocytes. The production of PDGF in platelets is upregulated by a group of agonists, including thrombin, collagen, ADP, and phorbol ester (Nguyen A, et al, 1998). PDGF secreted from platelets can initiate the process of SMC migration and proliferation. Subsequently, endothelial cells regenerated on the surface of neointima produce additional PDGF (Lefkovits J, et al, 1996). Besides, endothelial injury can stimulate the production of PDGF in SMC. Vascular cells-derived PDGF can further stimulate the proliferation of SMC in vascular wall (Deitch J S, et al, 1998). Antibodies against PDGF reduced 41% of neointimal area in rat arteries injured by balloon catheter (McGregor M, et al, 1999), which strongly suggests that PDGF plays an important role in injury-induced neointima formation. The present experiment for the first time demonstrate that hirulog-1 treatment reduces the abundance of PDGF in neointima of arteries injured by catheter. In comparison, the abundance of α-actin, one of the markers of SMC, was not obviously altered by hirulog-1 treatment. This shows that hirulog-1 specifically reduces the expression of PDGF in neointima, which can contribute to the effect of hirulog-1 or the deduction of injury-induced neointima formation.

Hirulog-1 treatment elongated aPTT in intact and catheter injured rats. This suggests that the effect of hirulog-1 on coagulation is not dependent on vascular injury. Although the effect of hirulog-1 on coagulation is transient, the decrease in thrombin generation can result in reduced platelet aggregation and PDGF generation. Pharmacological effects of hirulog-1 in other aspects can also contribute to haemostasis. In a separate experiment, hirulog-1 inhibited thrombin-induced production of plasminogen activator inhibitor-1 in vascular SMC (Hull R D, et al, 1992). Improvement of fibrinolytic activity due to reduced level of plasminogen activator inhibitor can reduce the tendency of thrombosis at injured sites.

Hirulog-1 is metabolized quickly in gastrointestinal tract, therefore, it is administrated through intravenous route. The plasma half-life of hirulog-1 is around 15-20 minutes (J Neurol Neurosurg Psychiatry, 1996), which is consistent with the time course of hirulog-1 on platelet deposition, and aPTT, and the requirement of multiple infusions of hirulog-1 to inhibit neointima formation. Additional inhibition of vascular stenosis can be achieved by prolonged infusion of hirulog-1. Gene transfer of hirulog analogue to vascular wall can be an alternative for preventing vascular restenosis, which potentially releases the thrombin inhibitor for days to weeks from selected locations in vascular tree. However, the present experiment examined the effects of hirulog-1 in rodents.

In summary, multiple intravenous infusions of hirulog-1 substantially reduced balloon catheter injury-induced neointima formation in rat carotid artery. The inhibitory effect of hirulog-1 on vascular stenosis is associated with decreased platelet deposition on denuded intima, coagulation activity and PDGF in neointima. Since hirulog-1 administration is relatively safe in humans (Lincoff A M, et al, 1993), this thrombin inhibitor can be considered as a candidate for the prevention of restenosis induced by vascular interventions.

Example 2

Hirulog-Like Peptide Reduces Balloon Catheter Injury-Induced Neointima Formation in Rat Carotid Artery Without Interference on Coagulation Activity Vascular restenosis is the major concern for the treatment of coronary heart disease (CHD) using vascular procedures. A number of drugs reduced neointima formation in vascular injury animal models and their application have been limited by systematic side effects. Hirulog-1 is a synthetic thrombin inhibitor. Clinical trials demonstrated that hirulog-1 reduced ischemic events in CHD patients. It caused less major bleeding complications compared to heparin but still increased the frequency of haemorrhage. Recent studies have demonstrated that hirulog-1 reduced balloon catheter-induced neointima formation in rats and atherosclerotic rabbits. A hirulog-like peptide (HLP) was designed which contains the active sites of hirulog-1 and a leading sequence to enhance the interaction between HLP and target cell surface proteins. Intravenous infusions of HLP reduced balloon catheter-induced increase in neointima/media ratio in rat carotid arteries by 33%. The levels of activated partial thromboplastin time during HLP infusion were significantly lower than during hirulog-1 infusion and close to that infused with saline. Besides, HLP suppressed the expression of platelet-derived growth factor in neointima. The results show that HLP reduces vascular injury-induced neointima formation in rats without obvious changes in coagulation activity. The effect of HLP on neointima formation can be, at least in part, due to its inhibition on the proliferative effect of thrombin in vascular cells.

Example 3

HLP is a designed synthetic peptide (FPESKATNATLD-PRPGGGGNGDFEEIPEEYLQ SEQ ID No:1, provisional patent Ser. No. 60/079,418). The carboxyl domain of HLP conserves the functional sites of hirulog-1 and hirudin (Lavie C J et al, 1990; Neuhaus K L et al, 1994). The unnatural amino acid in hirulog-1 is replaced by a 12 amino acid leading sequence mimicking a portion of N-terminal domain of the thrombin receptor. This is designed to enhance the inhibitory effect of HLP on the binding of thrombin to its receptor. The presence of the leading sequence can interfere the interactions between the inhibitor and the active site of thrombin. Ki of HLP for the enzymatic activity was two orders of magnitude greater than hirulog-1, which suggests that HLP is a weaker anticoagulant compared to hirulog-1 (Shen G X et al. unpublished observations). Previous experiments have demonstrated that infusion of HLP (1.6-3.2 mg/kg/hours for 4 hours started from 0.5 hours before the injury) reduced balloon catheter injury-induced neointima formation in rat carotid arteries by 36%. The preventive effect of HLP on neointima formation was comparable to equimolar amount of hirulog-1. The abundance of PDGF but not α-actin in neointima was significantly reduced by HLP treatment. The levels of aPTT and bleeding time were greatly increased during heparin infusion (50 U/kg/hours). One out of five rats died from haemorrhage during heparin infusion. HLP treatment did not cause haemorrhage, the elongation of aPTT or bleeding time compared to their basal levels. The effect of HLP on neointima formation in rat carotid artery lasted 6 months after the treatment. No significant change in bleeding time, liver and kidney functions was detected in rats 6 months after HLP treatment. Besides, HLP inhibited thrombin-induced DNA synthesis in cultured baboon aortic SMC. This shows that the effect of HLP is not limited to rats.

Influence of species variations on the assessment of therapeutic approaches for vascular restenosis. Rat carotid artery injury model is one of the most commonly used vascular injury models in small animals. Rats have very low levels of plasma LDL cholesterol and unsusceptible to diet-induced atherosclerosis (Liu L Y et al, 1996; Mueller D W et al, 1992). In uninjured rat arterial wall, medial SMC layer is covered by endothelium and virtually without intimal cellular layer. Neointima formation in rat arterial wall, induced by balloon injury, is not equivalent to restenosis due to lack of the complexity of atherosclerotic lesions. Agents successfully reduced intimal hyperplasia induced by balloon catheter injury in rats failed to be reproduced in human or larger animals with a few exceptions (Liu L Y et al, 1996). Rabbits develop atherosclerosis responding to high cholesterol diet. Balloon catheter injury or air desiccation accelerated the development of atherosclerosis in rabbits at pre-selected location (Liu L Y et al, 1996; Leveen R F et al, 1982). Anti-restenosis effect of several approaches in rabbits, but not all, were reproduced in clinical trials (Hehrlein C et al, 1994; Lafont A M et al, 1995). Dogs weakly respond to high cholesterol diet and are relatively resistant to atherosclerosis. Experimental manoeuvres, such as radiation, balloon injury, hypertension or hypothyroidism, are required for inducing atherosclerotic lesions in canine model (Liu L Y et al, 1996). Canine has not been widely accepted as a suitable model for the assessment of therapeutic approaches for restenosis. Cardiovascular system of swine is very close to human's and spontaneously develops atherosclerosis (Gal D et al, 1990). The predicative value for testing therapeutic approaches in swine is one of the greatest in all animal models (Ferrell M et al, 1992). Costs of boarding and drugs or animals (minipigs) in swine model are considerably high. Non-human primates are expected to be the most representative model for studying atherosclerosis due to extensive similarities in lipid metabolism, clotting system and the histology of atherosclerotic lesions with human. Commonly used non-human primate models for studying atherosclerosis and restenosis are rhesus and squirrel monkeys. The results generated from studies in monkeys are usually parallel to that in humans (Clarkson T B et al, 1995; Verlangieri A J, et al, 1992). However, some agents, such as modified heparin (astenose), inhibited restenosis in monkeys (Wilcox J N et al, 1994) but not in humans (Camenzind E et al, 1995). The usage of non-human primates has been limited by high costs of the animals and harmful viral infections (Wisler R W et al, 1966). In summary, there is no golden standard of animal model for the assessment of new approaches to prevent restenosis (Pratt R E et al, 1996). Rat model is acceptable for the initial screen of new approaches for economic consideration.

Early started multi-infusions of HLP can effectively reduce angioplasty-induced vascular restenosis in atherosclerotic rabbits without increase in bleeding tendency. The effect of HLP on the prevention of restenosis can partially result from its inhibition on cell proliferation, the expression of growth factors and/or fibrinolytic regulators in vascular wall. HLP is a suitable candidate for the prevention of vascular restenosis. The experiment examines the effect of HLP via intravenous route on angioplasty-induced restenosis in carotid artery of diet-induced atherosclerotic rabbits. The condition of HLP treatment for the prevention of restenosis is optimized. Safety and side effects of HLP are determined by short- and long-term follow-up studies. The influence of HLP on the expression of growth factors, fibrinolytic regulators and vascular cell proliferation in injured rabbit arterial wall are determined.

Previous studies demonstrated that HLP reduced neointima formation in rat carotid arteries induced by balloon catheter injury. The efficacy of HLP on angioplasty-induced restenosis in carotid artery is evaluated and the condition of HLP treatment is optimised in atherosclerotic rabbits.

Experimental Design

Animal model. New Zealand white rabbits (male, 3.5-4 kg) are anaesthetized by intramuscular injection using 40 mg/kg of ketamine, 5 mg/kg of xylazine and 0.8 mg/kg of acepromazine. Right carotid arteries are surgically exposed at aseptic condition. A segment of common carotid artery is temporarily clamped by microclamps. Endothelium in the segment of artery is injured by air desiccation as previously described (Muller D W et al, 1992). Briefly, a 23-gauge needle is inserted to clamped common carotid artery and penetrated through the upside of arterial wall to serve as a vent. After the needle is retracted, the lumen is flushed with saline. Vascular lumen is desiccated using nitrogen flow through a catheter in 80 ml/minutes for 8 minutes. Bleeding from needle puncture is stopped by non-occlusive compression (Leveen R F et al, 1982). Animals are returned to a cage and receive a diet containing 2% cholesterol and 6% peanut oil for 3 weeks. This diet is known to induce cell-rich fibrous plaques in rabbits (Kritchevesky D et al, 1976). Hypercholesterolemia is confirmed by measuring serum total cholesterol. Stenosis of carotid artery at injury site is verified by angiography. A PTCA catheter (3F) is inserted and centered across the stenosis. Angioplasty is performed 3-times by balloon inflation at 2 atm of pressure with 30 second intervals. The effectiveness of angioplasty is verified by angiography. Animals receive regular chow after angioplasty.

Pharmacological preparation. HLP (B.f) and hirulog-1 (Maraganore J M et al, 1990) are synthesized in Manitoba Institute of Cancer Research. The peptides are purified using high performance liquid chromatography to >85% of purity. Regular and LMW heparins are obtained from Leo Lab. Ltd. Reagents are freshly diluted with saline immediately before the experiments.

Dose-response. The experiments demonstrated that intravenous infusion of 1.6 mg/kg/hours of HLP for 4 hours started 0.5 hours before angioplasty moderately reduced restenosis in rabbits. According to the results of power analysis based on the variance of the preliminary data, each group should consist of 8-10 animals. Dose- and time-dependence of HLP on restenosis in atherosclerotic rabbits has not been systematically studied. The size of groups and concentration range for dose-response study is expanded in the present experiment. Atherosclerotic rabbits (3 weeks of high fat diet after air desiccation) are randomly divided into 6 groups. Animals receive 0.8, 1.6, 2.4, 3.2 and 4 mg/kg/hours of HLP through ear vein (n=10 for 2.4 and 4 mg/kg/hours, n=7 for other doses which were examined in smaller groups in the pilot study). Control group (n=10) receives saline in identical volume, speed and route. Half an hour after the start of the infusion, angioplasty is performed in the injured segment of carotid artery. Animals are maintained in supine position by additional injection of katamine (5 mg/kg) during the infusion. After four hours of infusion, animals are returned to a cage and receive a regular diet for four weeks before histological analysis of injured arteries. The results optimize the dose of HLP infusion for preventing restenosis in rabbits.

Time-dependence. The experiments in rabbits preliminarily compared the effects of single infusion with 1.6 mg/kg/hours of HLP for 2 hours and 4 hours. The results show that the efficacy of HLP can be further enhanced by the elongation of the infusion in rabbits. The effect of HLP on restenosis is also improved by increasing the frequency of the infusions. This is examined in two steps. First, atherosclerotic rabbits receive a single infusion of HLP for six or eight hours (n=10) in a dose optimized in I.2.3. Control group (n=10) receives an equal volume and speed of saline for identical period. Angioplasty is performed 0.5 hours after the initiation of the infusion. Secondly, atherosclerotic rabbits receive infusion of HLP in optimized dose for a length of period suggested from above experiment. The infusion is started at 0.5 hours before the injury and are repeated at 2nd or 2nd+3rd days (n=10) following angioplasty. Control groups with balloon injury (n=10) receive saline for identical period and frequency. The extents of restenosis in rabbits treated with HLP for various lengths is determined at 4 weeks after angioplasty.

Compare the effect of HLP with its functional or structural analogues. The effect of HLP has not been compared to its analogues in rabbits. The experiment examines the effects of hirulog-1, regular or LMW heparin in rabbits (n=10). Hirulog-1 is administered in equimolar amount for identical length and frequency as the condition of HLP optimized in above experiments. Regular or LMW heparin (50 U/kg/hours) is infused for an equal length and frequency as HLP. Control animals with balloon injury receive the same volume, speed and time of saline. The effects of hirulog-1 and heparin on restenosis is compared to that of HLP and vehicle controls at 4 weeks after angioplasty.

Long-term effect of HLP on restenosis. The effect of HLP treatment in optimized condition on restenosis in double-injury atherosclerotic rabbits is observed at 6-months after the treatment in a separate group (n=10). Control animals (n=10) receive the same volume and speed of saline for identical period. Histological analysis of injured arteries is performed 6 months after the treatment.

Histological analysis. Four weeks or six months after the angioplasty, injured carotid arteries are isolated following perfusion fixation with 4% paraformaldehyde. Continuous cross-sections of arteries are stained with haemotoxylin and erosin then examined under light microscopy. Sections show the greatest stenosis are subject to histological analysis of restenosis using the ratio of neointima/media area. Neointimal area represents the region between internal elastic lamina and residual lumen, and media area represents the region between external and internal elastic lamina.

Relationship between HLP concentrations and vascular response. The relationship between plasma concentrations and the anti-restenosis effect of HLP is analysed. Polyclonal antibodies against HLP-KLH conjugate were raised in rabbits by the applicants group. The antibodies specifically recognize HLP in plasma proteins using Western blotting analysis. A competitive immunoassay was developed to measure plasma levels of HLP. Relationship between the effect of HLP on restenosis and its blood concentrations is analysed, which helps evaluate the efficacy of HLP and the design of a proper regimen for HLP treatment to prevent restenosis.

Results. The results generated from above experiments demonstrate: i) that HLP infusion substantially reduces angioplasty-induced restenosis in atherosclerotic rabbits; ii) that regimen modification improves the efficacy of HLP; iii) optimized condition for prevents restenosis in rabbits by HLP; iv) difference between HLP and its analogues on the prevention of restenosis; v) long-term benefit of HLP on restenosis in atherosclerotic rabbits; v) relationship between blood concentrations of HLP and its anti-restenosis effect.

To Determine the Side Effects of HLP in Rabbits

Rationale: One of most important criteria to evaluate the potential of a new drug for the prevention of restenosis in stable patients is safety. Since HLP is a thrombin inhibitor, its impact on coagulation and haemorrhage is carefully evaluated. Previous experiments have indicated that HLP does not cause evident toxic effect in rats. The preliminary experiments suggest that HLP did not significantly change aPTT in rabbits. The effect of HLP on bleeding time or functions of vital organs in rabbits has not been observed. HLP is a polypeptide but its effects on immune reaction in rabbits remains unclear. This experiment examines the impact of HLP on haemorrhage, immune reactions, liver, kidney and myeloid functions in rabbits.

Experimental Design

Influence of HLP on coagulation and haemorrhage. The levels of aPTT and microvascular bleeding time is determined in atherosclerotic rabbits receiving HLP, heparin, hirulog-1 or saline. The effects of optimized HLP treatment on coagulation and haemorrhage is also be examined in a group of uninjured rabbits on regular diet (n=10). The levels of aPTT is determined in blood withdrawn at 15 minutes after the start of the infusions using MLA Coagamate XM system in Haematology Laboratory. Microvascular bleeding time is determined by bleeding from a cut on ear at 1 minutes after the initiation of infusion as previously described (Blajchman et al, 1979). Incidence of bleeding complications in rabbits with various treatments is recorded. Autopsy is applied to every animal, including unexpected death, to examine the sign of haemorrhage in various organs and tissues.

Impact of HLP on liver, kidney and myeloid functions. Peripheral blood is withdrawn before sacrifice from ear vein of normal or atherosclerotic rabbits with and without treatments for analysing complete blood counts, serum albumin, alanine transaminase and blood urea nitrogen (analysed in Dept of Clinical Chemistry) to determine the influence of HLP on liver, kidney and myeloid functions. HLP concentrations in blood is analysed to examine the relationship between blood concentrations and possible toxic effects of HLP.

Effect of HLP on immune reactions. Since HLP is a peptide, it potentially induces immune reactions. HLP is a weak antigen. HLP-KLH conjugate but not free HLP induced detectable antibodies in rabbits. The possibility of HLP induces immune reactions in rabbits has not been excluded. Blood is withdrawn four weeks or six months after angioplasty and treatment with HLP, its analogues or saline, and determine the levels of serum C-reactive protein (Clinical Chemistry). Antibodies against HLP in blood are detected by immunodiffusion. Allergic reaction to HLP is monitored during and after the treatment.

Results. The results generated from above experiments demonstrate that HLP at effective doses does not cause unfavourable side effects in haemostasis, immune, liver, kidney and myeloid systems in rabbits.

Influence of HLP on the expression of growth factors, fibrinolytic regulators and cell proliferation in arterial wall.

SMC is the major cellular component in neointima induced by balloon catheter injury. Other types of cells potentially presented in injured vascular wall, such as lymphocytes, macrophages, fibroblasts and EC, also potentially contribute to the development of restenosis. Vascular cells can generate multiple types of growth factors responding to excess thrombin. Overexpression of growth factors potentially stimulates cell proliferation in vascular wall. Recent studies demonstrated that PDGF receptor tyrosine kinase blocker inhibited angioplasty-induced restenosis in pigs (Banai S et al, 1998). The findings from the experiments indicated that hirulog-1 and HLP inhibited the expression of PDGF in neointima of rat carotid artery induced by balloon catheter injury and thrombin-induced DNA synthesis in baboon aortic SMC. The effects of HLP on cell proliferation and the expression of PDGF or other growth factors in rabbit vascular wall have not been studied. Tissue remodeling is likely to play a critical role in the development of restenosis. Plasmin is one type of protease implicated in tissue remodeling. uPA is likely involved in injury-induced neointima formation. Decreased PAI-1 activity in blood after PTCA was associated with reduced risk of restenosis (Huber K et al, 1993). TGF-β is a known PAI-1 agonist (Halstead J et al, 1995). Influence of growth factors, fibrinolytic regulators and their interactions on the development of restenosis has not been well understood. The present experiment investigates the effects of HLP on the expression of growth factors, fibrinolytic regulators and cell proliferation in rabbit vascular wall.

Experimental Design

Effect of HLP on the expression of growth factors in vascular wall. The expression of growth factors in injured and intact carotid artery are determined in atherosclerotic rabbits at 1 day, 1 week, four weeks and six months after receiving HLP, hirulog-1, heparin or saline (n=10). Cross-sections of injured and intact carotid arteries are subject to immunohistochemistry. After dewaxing, sections are pre-treated with hydroperoxide and trypsin to reduce non-specific binding. Subsequently, the section is incubated with commercially available antibodies against PDGF, HBEGF, bFGF or TGF-β (Santa Cruz, Sigma, Dakopatts or Calbiochem). Immunstain of antibodies is detected by biotinylated second antibodies and Histomark Orange system (Kirkegaard & Perry Lab) as previously described. The levels of various growth factors in tissue extracts from injured or intact carotid arteries are estimated using immunoassay kits for PDGF-AB, HBEGF, bFGF and TGF-β (R & D Systems) and normalized by total cellular proteins. The levels of the expression of the growth factors in injured and uninjured segments of carotid arteries from rabbits treated with HLP, its analogues or saline are compared. In order to answer the question which types of cells are associated with injury-induced expression of the growth factors, the types of cells in neointima expressing growth factors are identified using antibodies against cellular markers for SMC (mAb for α-actin, Sigma), EC (CD31, R & D system), macrophages and polymorphonuclear granulocytes (mAb for CD68, Santa Cruz), lymphocytes (mAb L11/135, ATCC) and fibroblasts (mAb 5B5 for prolyl-4-hydroxylase, Dakopatts), and double-staining as previously described (Hansson G K et al, 1991). The results indicate whether HLP treatment affect the expression of growth factors in injury induced neointima of rabbit carotid arteries and which types of cells are associated with the expression of the growth factors induced by injury.

Effect of HLP on cell proliferation. Cell proliferation in angioplasty injured arterial wall is determined in rabbits at 1 week, four weeks and six months after angioplasty and treatment with saline or HLP in optimized condition. Twenty-four hours before termination, 40 mg/kg of 5'-bromo-2'-deoxyuridine (BrdU) (Sigma) was injected intravenously to atherosclerotic rabbits received various treatments. BrdU incorporation to injured arterial wall is detected using mAb against BrdU (Sigma) followed by immunostaining. After fixation, DNA in a vascular wall is denaturated with HCl and Na2B4O7 then digested with pepsin. Nuclei in vessel sections positively stained with DNA interacting dye Hoechst 33528 (1 µg/ml) is visualized under microscopy (Wei G L et al, 1997). Labelling index is calculated as the percentage of BrdU stained nuclei versus total nuclei as previously described (Soma M R et al, 1998). BrdU uptake by intact arterial wall and by injured rabbits treated with saline are used as controls. Type of proliferating cells in vascular wall are identified by immunostaining with cellular markers as described. The correlation between cell proliferation and the expression of the growth factors in neointima is analysed.

Effect of HLP on the expression of fibrinolytic regulators in vascular wall. The expression of uPA, tPA and PAI-1 in injured carotid artery is examined at 1 day, 1 week, 4 weeks and 6 months after receiving HLP, hirulog-1, heparin or saline. The preliminary experiments shown that PAI-1, tPA and uPA in rabbit plasma were undetectable by ELISA kits for human uPA, tPA and PAI-1. Activity of uPA, tPA and PAI-1 in rabbit plasma are measured using substrate S-2390 (for PAI-1 and tPA) or S2444 (for uPA) (Kabi, Vitrum AB, Sweden) as previously described). The levels of those fibrinolytic regulators in protein extracts of injured and intact vascular tissue from animals treated with HLP, its analogues or saline are evaluated using Western blotting analysis with antibodies against rabbit tPA, uPA or PAI-1 (American Diagnostic) as previously described (Cockell K A et al, 1995). Correlation between the effect of HLP on restenosis and the expression of fibrinolytic regulators in neointima of carotid arteries of atherosclerotic rabbits is analysed.

Results. The results of above experiments indicate whether HLP alters the expression of growth factors, fibrinolytic regulators and cell proliferation in neointima induced by angioplasty, and whether those changes correlate to anti-restenosis effect of HLP in rabbits.

Statistics. The sizes of group is estimated by power analysis based the variance of preliminary data. Difference of data between two groups is compared using Student's t-test. For evaluating variances from more than two groups, one-way ANOVA and Sheffe's test are used. Single variable regression analysis and multiple variable stepwise regression analysis are analysed using SAS software.

Significance. The results of the experiment demonstrate the efficacy and safety of a new thrombin inhibitor, HLP, on the prevention of restenosis in carotid arteries of atherosclerotic rabbits, and provide insight to the cellular and molecular mechanism for the anti-restenotic effect of HLP. The information generated from this experiment provide an effective and safe approach for the pharmacological prevention of vascular restenosis induced by vascular procedures in CAD patients.

The results indicate that early started multi-infusions of HLP can effectively reduce angioplasty-induced vascular restenosis in atherosclerotic rabbits without significant side effect. The beneficial effect of HLP can result from its inhibition on cell proliferation, the expression of growth factors and/or fibrinolytic regulators in injured vascular wall. HLP is a potential alternative for the pharmacological prevention of vascular restenosis.

The effect of intravenous infusion of HLP on restenosis in carotid artery induced by double-injury (air desiccation+angioplasty) was investigated in diet-induced atherosclerotic New Zealand rabbits in comparison to its functional or structural analogues. Condition for HLP treatment on restenosis in rabbits was optimized.

The effects of HLP at therapeutic doses on coagulation, bleeding time, immune reactions, hematogenic, hepatic and renal functions was determined in normal and atherosclerotic rabbits through short- and long-term follow-up studies.

The effects of HLP on the expression of growth factors (PDGF, HBEGF, bFGF, TGF-β) and fibrinolytic regulators (uPA, tPA, PAI-1) in neointima of angioplasty-injured carotid artery of atherosclerotic rabbits was examined by immunoassay, Western blotting analysis, immunohistochemistry or biological activity assay. Cell proliferation in neointima of injured arteries was evaluated by in vivo 5'-bromo-2'deoxyuridine uptake.

The results of the experiment demonstrated the efficacy, side effects and potential mechanism for HLP treatment on the prevention of angioplasty-induced restenosis in atherosclerotic rabbits. The outcome of this experiment provides a safe approach for the prevention of restenosis in atherosclerotic cardiovascular disease patients receiving therapeutic vascular procedures.

Example 4

Hirulog-like peptide (HLP) was rationally designed to enhance the inhibition on the binding of thrombin to its receptor with less interruption on coagulation activity in comparison to hirulog-1. Single infusion of HLP for 4 hours started 0.5 hours before balloon catheter injury reduced neointima formation by 36% in rat carotid artery compared to vehicle controls. Tail bleeding time and activated partial thromboplastin time during HLP infusion were not significantly different from vehicle controls, but were significantly shorter than that during heparin or hirulog-1 infusion. HLP treatment attenuated the expression of platelet-derived growth factor (PDGF) in the neointima of injured arteries. HLP also inhibited thrombin-induced thymidine incorporation in cultured baboon aortic smooth muscle cells (SMC). The findings suggest that HLP can substantially inhibit balloon catheter injury-induced neointima formation without noticeable increase in bleeding tendency in rats. The inhibition of HLP on the expression of PDGF and SMC proliferation in vascular wall potentially contributes to the preventive effect of the thrombin inhibitor on injury-induced neointima formation in vascular wall.

A thrombin inhibitor, hirulog-like peptide (HLP), was designed to improve the safety of synthetic thrombin inhibitors. The HLP was examined for the efficacy of HLP on the prevention of balloon catheter injury-induced neointima formation in carotid artery in rat model. The impacts of HLP on the expression of PDGF in rat vascular wall and the proliferation of cultured baboon aortic smooth muscle cells (SMC) were investigated.

Methods

Vascular Injury Model

Rat carotid artery balloon injury model was prepared as previously described (Lincoff et al, 1993). Male Sprague-Dawley rats (380-420 g) on regular chow were anaesthetized by intraperitoneal injection with 75 mg/kg of ketamine hydrochloride (MTC Pharmaceutics Cambridge, ON) plus 5 mg/kg of xylazine (Bayer Inc., Etobicoke, ON), and maintained by intravenous infusion of ketamine (60 mg/kg/h) via femoral vein through a peristaltic pump for 4 hours. Right external carotid artery was ligated at the level of mandible by silk. Proximal common and internal carotid arteries were temporarily clamped. An incision was made on proximal external carotid artery. Arterial embolectomy catheter (size 2F, Baxter, Irvine, Calif.) was inserted through the incision into the common carotid artery. Endothelial denudation was achieved by mechanically pulling intermittently inflated balloon catheter at 3 atm pressure for 5-times within 1-1.5 cm distance in the lumen of proximal common carotid artery (Libby P et al, 1992).

Pharmacological Treatment

HLP (FPESKATNATLDPRPGGGGNGDFEEIPEEYLQ SEQ ID No:1, Provisional Patent No. 60/193,114) was designed based on the sequences of hirulog-1 and the thrombin receptor (Clowes A W et al, 1991, Narins C R et al 1998). Hirulog-1 was prepared as previously described (Clowes A W et al, 1991, Lincoff A M et al, 1993). The synthesized peptides were purified by high performance liquid chromatography and freshly dissolved in saline. Heparin was obtained from GIBCO BRL (Burlington, ON). Intravenous infusions of various agents dissolved in saline were administered via femoral vein using a peristaltic pump in a speed of 2.5 ml/h. Rats were intravenously infused with 50 U/kg/h of heparin, 1 mg/kg/h of hirulog-1, 1.6 mg/kg/h (equal molar amount as 1 mg/kg/h of hirulog-1) or 3.2 mg/kg/h of HLP. The infusions were started at 0.5 hours before the balloon injury. Control animals received saline in equal volume and speed via matching route.

Histological Analysis

Rat vasculature was infused with 100 ml of saline then with 300 ml of 4% formaldehyde in phosphate buffered saline (PBS) at 100 mmHg of pressure. Right common carotid arteries were surgically isolated and immersed in 4% formaldehyde for up to 2 weeks then embedded in paraffin (Lincoff et al., 1993). Cross-sections of vascular tissue in 5 μm thickness were mounted on glass slides and stained with haematoxylin and eosin. Continuous sections from injured fragment of each vessel were photographed under light microscopy to identify maximal vascular stenosis for morphological analysis. The following definitions were used in morphological analysis: a) residual lumen, vascular lumen formed after injury; b) media area, area between external and internal elastic lamina; c) neointimal area, area between internal elastic lamina and residual lumen; d) neointima/media, the ratio of neointimal area/media area; e) stenosis (%), the percentage of neointimal area/(residual lumen+neointimal area) (Scwartz S M et al, 1996).

Immunohistochemistry

Cross-sections of carotid artery embedded in paraffin were dewaxed using xylene then hydrated by decreasing concentrations of ethanol. The sections were treated with 10% hydroxyperoxide then with 0.05% trypsin to reduce non-specific binding. After rinsing with PBS, the sections were treated with 10% goat serum in PBS for 20 minutes then incubated with rabbit polyclonal antibodies against human PDGF and cross-reacting with rat PDGF (Calbiochem, Cambridge, Mass.), monoclonal antibody against mouse SMC α-actin (Sigma, St. Louis, Mo.) or non-specific rabbit IgG at 4° C. overnight (Lincoff et al., 1993). Subsequently, the sections were treated with appropriate biotinylated second antibodies for 30 minutes at room temperature then with streptavidin peroxidase. The binding of antibody to antigen was visualized by Histomark Orange system (Kirkegaard and Perry Laboratories, Gaithersburg, Md.) (Lincoff et al., 1993). Immunostaining areas on images were semi-quantified by integration and expressed in percentage of total area of neointima as previously described (Popma J J, et al, 1993, Carmeleit P, et al, 1997, Lincoff A M et al, 1993).

Activated Partial Thromboplastin Time (aPTT) and Bleeding Time

The levels of aPTT in plasma were analyzed using MLA 1000C Coagamate XM system in Haematology Laboratory, Health Sciences Centre, Winnipeg. For the evaluation of bleeding time, 1 mm of tail tip was removed using a razor blade. Resultant wound was gently blotted with filter paper immediately after the cut and each 30-second thereafter until bleeding stopped. Periods between cutting and no blood blotted onto filter paper were defined as bleeding time (Ishiwata S et al, 1997, 20).

3H-Thymidine Incorporation Assay

Baboon aortic SMCs (seed cells provided by Dr. A. W. Clowes, University of Washington, Seattle) were grown as previously described (Ishiwata S et al, 1999) and seeded in 12-well plates to sub-confluence. Sub-confluent cells were incubated with serum-free medium for 48 hours. Quiescent SMCs were stimulated with medium containing 1% fetal calf serum and 10 U/ml of thrombin in the absence and presence of HLP for 4 hours. The incubation was continued following the replacement of fresh medium supplemented with 10% serum in the absence of thrombin or its inhibitor for 14 hours. Finally, SMCs were incubated with 0.1 µCi/ml of 3H-thymidine (NEN, Boston, Mass.) in medium containing 10% of serum for 6 hours. At the end of the incubation, the cells were thoroughly washed with PBS then 5% ice-cold trichloroacetic acid, and harvested in 0.25 N NaOH (Safian R D et al, 1990). Radioactivity in aliquots of cell lysate was analyzed in scintillation counter. 3H-Thymidine incorporation was assessed by radioactivity in cell lysates following adjustment with cellular proteins in each well.

Statistics

Student's t-test was used for the comparisons of probabilities between two groups. One way ANOVA analysis plus Scheffe's test were performed for the comparisons between multiple groups. Group sizes were indicated by the numbers (n) of animals or the wells of cultured cells in each group. The level of significance was defined as $p<0.05$.

Results

Effect of HLP on Balloon Injury-Induced Neointima Formation

Balloon catheter dilation induced obvious increase in the thickness of neointima of carotid artery wall and the narrowing of vascular lumen (FIG. 1B). The formation of neointima in injured carotid artery, indicated by neointimal area, neointima/media and stenosis, was obviously reduced at 2 weeks following the treatment with heparin, hirulog-1 or HLP compared to injured animals receiving saline or vehicle controls (FIG. 2). Neointimal area in injured carotid artery of rats was reduced by treatment with 50 U/kg/h of heparin (19%, $p<0.01$), 1 mg/kg/h of hirulog-1 (31%, $p<0.01$), 1.6 mg/kg/h (31%, $p<0.01$) or 3.2 mg/kg/h of HLP (29%, $p<0.05$) compared to saline-treated control animals (FIG. 2, upper). The levels of neointima/media ratio and stenosis were also significantly reduced by treatment with heparin, hirulog-1 or HLP compared to vehicle controls ($p<0.05$ or 0.01, FIG. 2, middle and bottom). The levels of neointimal area (except HLP3.2 group), neointima/media and stenosis in injured rats treated with HLP or hirulog-1 were significantly lower than that in heparin-treated rats ($p<0.05$ or 0.01) (FIG. 2).

Influence of HLP on Coagulation Activity and Bleeding Tendency

Coagulation activity was evaluated by measuring aPTT in blood at 5 minutes after the start of the infusion. The levels of aPTT was prolonged by 4- to 5-fold during the infusion of 50 U/kg/h of heparin ($p<0.05$). Hirulog-1 treatment (1 mg/kg/h) elongated aPTT by 2- to 3-fold ($p<0.01$). The lengths of aPTT in rats during infusion with HLP in equal or double molar amounts of 1 mg/kg/h of hirulog-1 were shorter than that during heparin or hirulog-1 treatment ($p<0.01$) and did not significantly differ from that of control group (Table 1). Bleeding tendency in rats following various treatments was estimated by tail bleeding time at 10 minutes after the initiation of the infusions. Heparin or hirulog-1 treatment significantly prolonged tail bleeding time ($p<0.05$ or 0.01). Tail bleeding time in HLP-treated rats was not significantly different from controls, but shorter than that in animals treated with heparin- or hirulog-1 ($p<0.05$, Table 1).

Impact of HLP on the Expression of PDGF in Neointima

The expression of PDGF in carotid arterial wall with and without balloon catheter injury was immunohistochemically examined using specific antibodies. In arterial walls without injury, the binding of PDGF antibodies to the media layer of arterial wall was negligible (FIG. 3C). In comparison, the expression of α-actin was detected in the medial layer of arterial wall without injury. Catheter injury induced increases in the immunostain of PDGF and α-actin in the neointima of injured carotid artery (FIG. 3E, F). Heparin did not noticeably alter the abundance of PDGF or α-actin (FIG. 3H, I). Infusion of hirulog-1 or HLP significantly reduced the abundance of PDGF in neointima ($p<0.01$), but did not significantly affect the expression of α-actin (Table 2). Comparable results were obtained from four independent experiments.

Effects of HLP on Thymidine Incorporation in Cultured Primate Arterial SMC

PDGF is a potent mitogen for vascular SMC. In order to answer the question whether HLP inhibits SMC proliferation, the effect of HLP on thrombin-induced thymidine incorporation was examined in cultured baboon aortic SMC. Thrombin (10 U/ml) increased 3H-thymidine incorporation in baboon aortic SMC by 43% ($p<0.01$). Treatment with 20 µM HLP significantly reduced thrombin-induced increase in 3H-thymidine incorporation in SMC ($p<0.05$) compared to cells treated with thrombin only ($p<0.05$). HLP alone up to 20 µM did not significantly alter 3H-thymidine incorporation in baboon aortic SMC (FIG. 4).

Long-Term Effects of HLP

Impact of HLP on balloon injury-induced neointima formation was also determined in rats at 6 months after the treatment. Two groups of rats with balloon injury in carotid artery were infused with 1.6 mg/kg/h of HLP or equal volume of saline for 4-hours started from 0.5 hours before the injury. In the rats treated with HLP, neointima/media ratio in injured segments of carotid artery at 6 months after the treatment was significantly lower than that in vehicle controls (1.30±0.04 versus 0.90±0.07, $p<0.001$). No significant difference was found in tail bleeding time, alanine transaminase or blood urea nitrogen between HLP-treated and control groups at 6 months after the treatments.

Discussion

The results of the present experiment demonstrated that early started intravenous infusion of HLP substantially reduced balloon catheter injury-induced neointima formation in rat carotid artery without significant change in coagulation activity or bleeding tendency. The findings show that HLP is an effective and safe drug for the prevention of vascular neointima formation induced by balloon catheter injury in rat model.

HLP keeps the sequence of the active sites of hirulog-1. The amino-terminal tail of HLP contains a region which is homology to a distal portion of the extracellular domain of the thrombin receptor. This region of HLP is structurally distinct from hirulog-19-20 (or HLP20-31) which aims the anion binding exosite of thrombin (Carmeliet P et al, 1997). HLP provides double-site of inhibition on the binding of thrombin to the thrombin receptor, which can more effectively reduce the activation of the thrombin inhibitor and the cellular effects of thrombin. In addition, the amino-terminal sequence of HLP can affect the interaction of the inhibitor with the active site of thrombin in a manner different from hirulog-1. This structural difference between HLP and hirulog-1 on their amino terminal can partially explain the lower inhibition of HLP on coagulation. The amino terminal of HLP can be slowly cleaved by thrombin after the formation of complex with thrombin as hirulog-1 (Buchanan M R et al, 1999), which prevents the complete consumption of thrombin. Ki of HLP on the enzymatic activity of thrombin was two orders of magnitude greater than hirulog-1 (Lefkovitis J et al, 1997) using α-thrombin and spectrozyme (American Diagnostica Inc., Greenwich, Conn.) as a substrate for thrombin (Shen et al. unpublished observations).

The results generated from the present experiment demonstrated that the effective doses of HLP did not prolong aPTT or bleeding time in rats compared to heparin or hirulog-1. These findings show that HLP is a weaker anticoagulant than hirulog-1. The relatively better safety profile of HLP compared to other thrombin-specific inhibitors permits its administration in higher doses, which provides HLP an efficacy advantage.

Previous studies demonstrated that early started and prolonged infusions of hirudin improved its effect on the prevention of angioplasty-induced restenosis in atherosclerotic rabbits (Vu T K et al, 1991). The earlier studies indicated that multiple infusions of hirulog-1 (1 mg/kg/h for 4 hours×6-times) but not single or twice of infusions significantly reduced balloon injury-induced neointima formation in rats (Lincoff et al., 1993). The main difference between the procedures of hirulog-1 administration between the earlier and the present experiment is interval between balloon injury and the start of the infusion. In the earlier study, the infusion of hirulog-1 was started immediately (within two minutes) after balloon injury (Lincoff et al., 1993). In the present experiment, infusion of hirulog-1 or HLP initiated at 0.5 hours before the injury.

Figure 2:
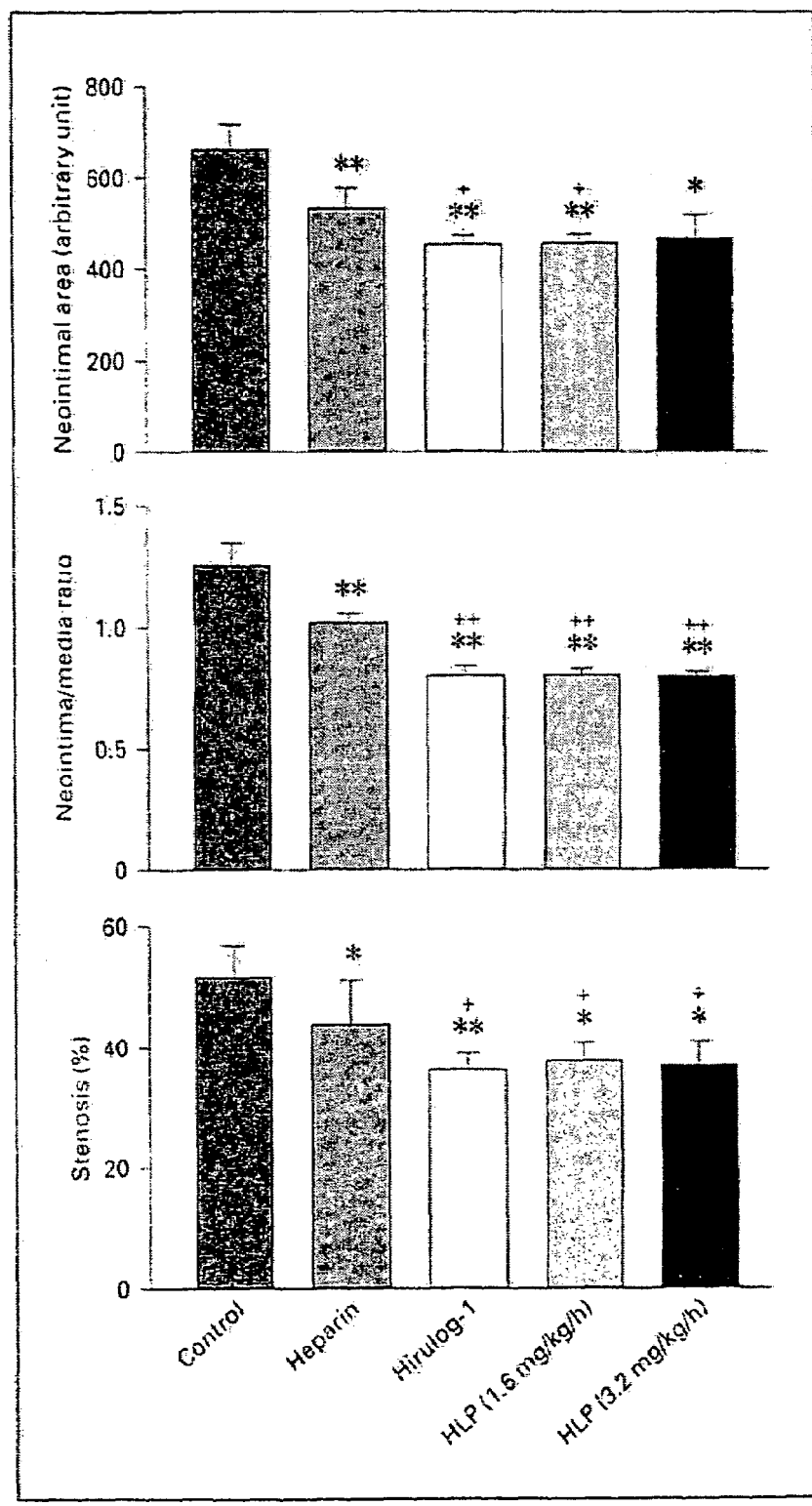
FIGS. 2 A, B, C show the comparison of the effects of HLP, hirulog-1 and heparin on neointima formation in vascular stenosis and rat carotid artery induced by a balloon catheter injury.

The early started single infusion of hirulog-1 substantially reduced balloon catheter injury-induced neointima formation compared to vehicle controls (FIGS. 1 and 2). Large amounts of thrombin are expected to be released rapidly after the balloon injury. Administration of thrombin inhibitors after the injury is not sufficient to block the early effects of thrombin in excess amounts. Administration of thrombin inhibitors prior to the injury more efficiently prevent the activation of the coagulation cascade and the cellular effects of thrombin compared to the infusions started after the injury. The results of the experiments provide additional evidence that pre-treatment of thrombin inhibitors started before vascular procedures can improve the efficacy on the prevention of injury-induced neointima formation in vascular wall.

Thrombin is a potent stimulant for the expression of PDGF (Liu L Y et al, 1996). Previous studies indicated that antibodies against PDGF reduced neointima formation by 40% in rat arteries injured by balloon catheter (Maresta A et. al, 1994). Multiple infusions of hirulog-1 reduced the expression of PDGF in neointima of rat carotid artery (Lincoff et al., 1993). The results of the present experiment demonstrated that the infusions of hirulog-1 with equivalent doses and time but started before balloon injury substantially suppressed the later expression of PDGF in the neointima of carotid artery induced by balloon injury. It shows that early inhibition of thrombin in blood circulation by the thrombin inhibitor provides more efficient prevention on injury-induced expression of PDGF in vascular wall as well as neointima formation. PDGF stimulates the proliferation of vascular SMC (Ferns G A et al, 1992). The present experiment examined the effect of HLP on the proliferation of arterial SMC from primates. HLP inhibits thrombin-induced SMC proliferation in cultured baboon aortic SMC. The anti-proliferative effect of HLP can result from its inhibition on the expression of PDGF induced by thrombin, which possibly contributes to the attenuation of injury-induced neointima formation following treatment with the inhibitor.

The effect of HLP on injury-induced neointima formation has only been investigated in rat model. Previous experiments demonstrated that a number of approaches inhibited balloon injury-induced neointima formation in rats, but the effects failed to be reproduced in human or larger animal models (Vermylen J, 1995). One of possible interpretations for those findings is the low levels of low density lipoproteins and relative atherosclerosis-resistance in rats compared to atherogenic animals (Vermylen J, 1995). Further investigations on the efficacy of HLP in atherogenic animals, such as swine, rabbits or non-human primates, can provide helpful information for evaluating the potential of HLP in the prevention of restenosis. The findings of the present experiment on the inhibitory effect of HLP on thymidine incorporation show that the effects of HLP are not limited to rats.

More specifically, FIG. 1 shows the effect of hirulog-like peptide (HLP) on balloon catheter injury-induced neointima formation in rat carotid arteries. FIG. 1A shows no injury. FIG. 1B-F shows the right carotid artery injured by balloon catheter and intravenously infused with following reagents; B: saline; C: 50 U/kg/h of heparin; D: 1 mg/kg/h of hirulog-1; E: 1.6 mg/kg/h of HLP (equimolar amount as 1 mg/kg/h of hirulog-1); F: 3.2 mg/kg/h of HLP. The infusions were started at 0.5 hours before the injury and lasted for 4 hours. Two weeks after the injury, right common carotid arteries were surgically isolated. Cross-sections of arterial fragments on slides were stained with haematoxylin and eosin then photographed under light microscopy (×40).

FIG. 2 shows the comparison of the effects of HLP, hirulog-1 and heparin on neointima formation and vascular stenosis in rat carotid artery induced by balloon catheter injury. Right carotid arteries of rats were injured by balloon catheter. Infusions with following agents were started from 0.5 hours prior to the injury and lasted for 4 hours via femoral vein. Control was as follows: saline (n=7 of animals); heparin: 50 U/kg/h; hirulog-1: 1 mg/kg/h; HLP(1.6): 1.6 mg/kg/h; HLP (3.2): 3.2 mg/kg/h (n=4 of animals). Right common carotid arteries were isolated at 2 weeks after the injury and stained with haematoxylin/eosin then photographed under microscopy. Morphological analyses were performed, as described in the Methods, wherein upper is the Neointimal area, middle is the neointima/media ratio and bottom is the stenosis (%).

Values were expressed in mean±SD. *,**: p<0.05 or 0.01 versus control group; +,++: p<0.05 or 0.01 versus heparin group.

Figure 3:
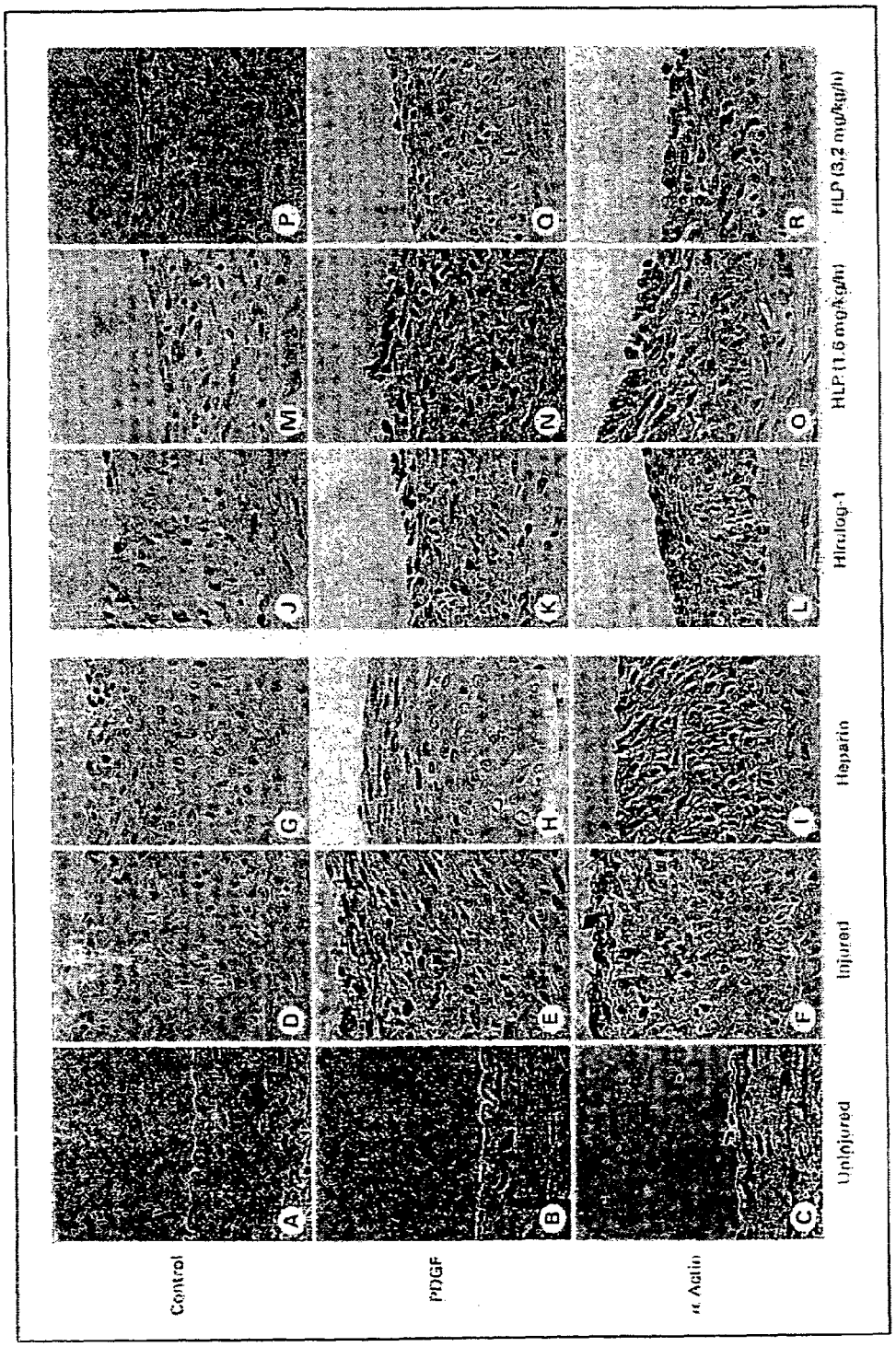
FIGS. 3 A-R show the effects of HLP on the expression of PDGF and α-actin in neointima of rat carotid artery wall following balloon injury.

FIG. 3 shows the effects of HLP on the expression of PDGF and α-actin in neointima of rat carotid arterial wall following balloon injury. Right common carotid arteries of rats were injured by balloon catheter. The rats were intravenously infused with saline, 50 U/kg/h of heparin, 1 mg/kg/h of hirulog-1, 1.6 mg/kg/h (1.6) or 3.2 mg/kg/h (3.2) of HLP for four hours started from 0.5 hours before the injury. Injured carotid arteries were isolated two weeks after the treatments. Vascular sections were proceeded for immunohistochemistry with antibodies against PDGF, α-actin or non-specific rabbit serum IgG.

Sections were examined under light microscopy (×160). FIG. 3A-C shows uninjured sections, D-F show infused sections with saline, G-I show heparin, J-L show hirulog-1, M-O shows HLP1×, and P-R show HLP2×. (A, D, G, J, M, P: non-specific IgG; B, E, H, K, N, Q: PDGF; C, F, I, L, O, R: α-actin.)

FIG. 4 shows the effect of HLP on thrombin-induced 3H-thymidine incorporation in baboon aortic SMC. Quiescent cells were incubated with 0-20 μM HLP in the presence or absence of 10 U/ml of thrombin in medium containing 1% serum for 4 hours, followed by incubation with medium containing 10% serum for 14 hours, then with 0.1 μCi/ml of 3H-thymidine for 6 hours. Values were expressed in mean±SD from quadruplicate-wells. (*,**: p<0.05 or 0.01 versus dose-matched control; +: p<0.05 versus culture treated with HLP alone.)

In summary, early started intravenous infusion of HLP reduced neointima formation in rat carotid artery induced by balloon catheter injury, that was not associated with an increase in bleeding tendency. The beneficial effect of HLP on injury-induced vascular neointima formation results from its inhibition on the expression of growth factors and SMC proliferation.

Example 5

Hirulog-Like Peptide Reduces Balloon Catheter Injury Induced Restenosis in Rabbits Carotid Artery.

Restenosis is responsible for the 30-40% long term failure rate following coronary revascularization. Thrombin inhibitors have been considered as one type of potential drug for the prevention of restenosis. Previous studies in the laboratory demonstrated that a new thrombin specific inhibitor, hirulog-like peptide (HLP) reduced balloon catheter induced neointima formation in rat carotid arteries. The experiment was designed to examine the effect of HLP on restenosis of carotid arteries in atherosclerotic rabbits. Right carotid arteries of male New Zealand rabbits were subjected to air dessication. After the endothelium injury, the rabbits received a hypercholesterol and fat diet (2% cholesterol+6% peanut oil) for three weeks. Stenosis in right carotid arteries was dilated using a 3.0 mm diameter coronary dilation catheter. The rabbits were returned to a regular diet and the carotid arteries were harvested at four weeks after the angioplasty. Intravenous infusion of HLP (0.8 mg/kg/h for four hours, n=7) started 0.5 hours before angioplasty, which reduced neointima formation by 60% (0.28±0.16 vs. saline control 0.71±0.52, mean±SD. p>0.05), stenosis by 38% (0.42±0.19 vs. control 0.68±0.17, p<0.05 and neointima/media by 62% (0.58±0.32 vs. control 1.55±0.88, p<0.05) in balloon catheter-injured carotid arteries compared to control rabbits with identical injuries but infused with saline (n=6). Activated partial thromboplastin time in HLP treated rabbits was not significantly prolonged compared to saline controls. None of HLP treated rabbits suffered from bleeding complications. The results show that HLP inhibits angioplasty induced restenosis without noticeable interruption of coagulation activity in rabbits.

Throughout this application, various publications, including United States patents, are referenced by author and year and patents by number. Full citations for the publications are listed herein. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention as described herein are possible in light of the above teachings and Examples. It is, therefore, to be understood that-within the scope of the described invention, the invention can be practiced otherwise than as specifically described.

TABLE 1

Effects of HLP and its functional and structural analogues on aPTT and bleeding time in rats

| Treatments | aPTT (second) | Bleeding time (min) |
|---|---|---|
| Control | 19.43 ± 3.43 | 14.25 ± 0.65 |
| Heparin | 92.83 ± 18.12* | 22.38 ± 4.05* |
| Hirulog-1 | 52.38 ± 2.84**+ | 21.88 ± 1.55** |
| HLP(1.6) | 20.80 ± 3.24++xx | 16.37 ± 1.55+x |
| HLP(3.2) | 19.80 ± 1.65++xx | 16.50 ± 1.58+x |

Rats with balloon catheter injured carotid artery were intravenously infused with saline (control), 50 U/kg/h of heparin, 1 mg/kg/h of hirulog-1, 1.6 mg/kg/h of HLP [HLP(1.6)] or 3.2 mg/kg/h of HLP [HLP(3.2)] for 4 hours started from 0.5 hours before the injury. aPTT was determined at 5 minutes after the start of the infusion. Determination of tail bleeding time was started at 10 minutes after the initiation of the treatment. Values were expressed in mean±SD (n=4 of animals). *, **: p<0.05 or <0.01 versus controls. +, ++: p<0.05 or <0.01 versus heparin, x, xx: p<0.05 or <0.01 versus hirulog-1.

TABLE 2

Effects of HLP on the abundance of PDGF and α-actin in the neointima of rat cartoid artery induced by balloon catheter injury

| | | Area of immunostain (% of total area) | |
|---|---|---|---|
| Treatments | Non-specific IgG | α-Actin | PDGF |
| Control | UD | 51.02 ± 1.13 | 50.38 ± 2.06 |
| Heparin | UD | 50.81 ± 0.46 | 48.03 ± 2.16 |
| Hirulog-1 | UD | 50.40 ± 1.63 | 37.23 ± 0.72*+ |
| HLP(1.6) | UD | 51.23 ± 1.09 | 34.04 ± 1.73*+ |
| HLP(3.2) | UD | 50.02 ± 1.28 | 34.65 ± 2.05*+ |

Rats with balloon catheter injured carotid artery were treated as follows; saline (control); 50 U/kg/h of heparin, 1 mg/kg/h of hirulog-1, 1.6 mg/kg/h of HLP [HLP(1.6)] or 3.2 mg/kg/h of HLP [HLP (3.2)] for 4 hours started from 0.5 hours before the injury. UD: undetectable. Values were expressed in mean±SD (n=4 of animals). *: p<0.01 versus controls. +: p<0.01 versus heparin.

REFERENCES

1. Fenton II. J W, Ofusu F A, Brezbiak D V, Hassouna H I. Thrombin and antithrombotics. Semin Thromb Haemost. 1998, 24:87-91.
2. Esmon C T. Protein-C: biochemistry, physiology and clinical implication. Blood 1983;62:1155-8.
3. Nguyen A, Gemmell C H, Yeo E L, Packham M A, Rand M L. Ethanol inhibits thrombin-induced secretion of the contents of human platelet dense and alpha-granuales and lysosomes. Thromb Haemost 1998;80:662-7.
4. Ross R, Raines E W, Bowen-Pope D. The biology of platelet-derived growth factor. Cell 1986;46:155-169.
5. Stouffer G A, Rurge M S: The role of secondary growth factor production in thrombin-induced proliferation of vascular smooth muscle cells. Semin Thromb Haemostat 1998;24:145-50.
6. Huang R, Sorisk A, Church W R, Simons E R, Rittenhouse J. "Thrombin" receptor-directed ligand accounts for activation bu thrombin of platelet phospholipase C and accumulation of 3-phosphrylated phosphoinosides. J Biol Chem 1991;266:18435-8.
7. Rasmussen U B, Vouret-Craviari V, Jallat S, Schlesinger Y, Pages G, Paviranit A, Lecocq J P, Ponyssegur J, Van Obberghen-Schilling E. cDNA cloning and expression of a hamster alpha-thrombin receptor coupled to Ca2+ mobilization. FEBS Lett 1991;288:123-8.
8. Vu T K, Hung D T, Whenton V I, Coughlin S R. Molecular cloning of a functional thrombin receptor reveals a novel proteolytic-mechanism of receptor activation. Cell 1991; 64:1057-68.
9. Shen G X, Ren S, Fenton J W II. Transcellular signaling and pharmacological modulation of thrombin-induced production of plasminogen activator inhibitor-1 in vascular smooth muscle cells. Semin Thromb Haemost 1998;24: 151-6.
10. Ren S, Cockell K A, Fenton II J W, Angel A, Shen G X. G protein and phospholipase C mediate thrombin-induced generation of plasminogen activator inhibitor-1 from vascular smooth muscle cells. J Vasc Res 1997;34:82-9.
11. Ryan T J, Faxon D P, Gunnar R M, Kennedy J W, King S B III, Loop F D, Peterson K L, Reeves T J, Williams D O, Winters W L Jr, Fisch C, DeSanctis R W, Dodge H T, Weinberg S L. Guidelines for percutaneous transluminal coronary angioplasty. A report of the American College of Cardiology/American Heart Association Task Force on Assessment of Diagnostic and Therapeutic Cardiovascular Procedures (Subcommittee on Percutaneous Transluminal Coronary Angioplasty). J Am Coll Cardiol. 1988;12:52945.
12. Lincoff A M, Topol E J, Chapekis A T, George B S, Canela R J, Muller D W. Zimmerman C A, Ellis S G. Intracoronary stenting compared with conventional therapy for abrupt vessel closure complicating coronary angioplasty: a matched case-control study. J Am Coll Cardiol 1993;21:866-75
13. Libby P, Schwartz D, Brogi E, Tanaka H, Clinton S K. A cascade model for restenosis. A special case of atherosclerosis progression. Circ. 1992;86(Suppl III): III-47-52.
14. Clowes A W, Reidy M A. Prevention of stenosis after vascular reconstruction: pharmacologic control of intimal hyperplasia—A review. J Vas Surg. 1991; 13:885-91.
15. Narins C R, Holemes D R, Topol E J. A call for provisional stenting. The balloon is back. Circ 1998;97:1298-305.
16. Scwartz S M, Reidy M A. Restenosis. An assessment of factors important in arterial occlusion in Atherosclerosis and Coronary Artery Disease. Edited by V. Fuster, R. Ross and E. J. Topol. Lippincott-Raven Publishers, Philadephia 1996, p:701-14.
17. Popma J J, Salter L F, Pichard A D, Kent K M, Campell A, Chunag Y C, Merritt A J, Bucher T A, Leon M B. Vascular complications after balloon and new device angioplasty. Circ 1993;88: 1569-78.
18. Carmeleit P, Moons L, Dewerchin M, Ploplis V, Plow E, Collen D. Impaired arterial neointima formation in mice with disrupted plasminogen gen. J Clin Invest 1997;99: 200-8.
19. Ishiwata S, Tukada T, Nakanishi S, Nishiyama S, Seki A. Postangioplasty restenosis: platelet activation and the coagulation-fibrinolytis system as possible factors in the pathogenesis of restenosis. Am Heart J 1997;133:387-92.
20. Ischinger T A. Antithrombiotics in interventional cardiology: optimizing treatment and strategies. Am J Cardiol 1998;82:25L-28L.
21. Ishiwata S et al 1997, Tsakirirs D A, Tschopl M, Jager K, Haefeli W E, Wolf F, Marbet G A. Circulating cell adhesion molecules and endothelial markers before and after transluminal angioplasty in peripheral arterial occlusive disease. Atherosclerosis 1999; 142:193-200.
22. Safian R D, Gelbfish J S, Emy R E, Schnitt S J, Schmidt D A, Baim D S. Coronary atherectomy. Clinical, angiographic, and histological findings and observations regarding potential mechanisms [see comments]. Circ 1990;82: 69-79.
23. Carmeliet P, Collen D. Molecular genetics of the fibrinolytic and coagulation systems in haemostasis, thrombogenesis, restenosis and atherosclerosis. Cur Opin Lipidol 1997;8:118-25.
24. Buchanan M R, Brister S J. A rationale for targeting antithrombotic therapy at the vessel wall: improved antithrombotic effect and decreased risk of bleeding. Wien Klin Wochenschr 1999;111:81-9.
25. Lefkovitis J, Topol E J. Pharmacological approaches for the prevention of restenosis after percutaneous coronary intervention. Prog Cardiovasc Dis 1997;40:141-58.
26. Liu L Y, Dai E, Hobman L M, Kolodziejczyk M D, Lucas A. Animal models of restenosis: myth or reality. Cur Pharmaco Design 1996;2:553-84.
27. Maresta A, Balducelli M, Cantini L, Casari A, Chioin R, Fabbri M, Fontanelli A, Monici Preti P A, Repetto S, De Servi S et al. Trapidi (triazolopyrimidine), a platelet-derived growth factor antagonist, reduced restenosis after percutaneous transluminal coronary angioplasty. Results of the randomized, double-blind STARC study. Studio Trapidil versus Aspirin nella Restenosi Coronarica. Circ 1994; 90:2710-5.
28. Ferns G A, Forster L, Stewart-Lee A, Konneh M, Nourooz-Zadeh J, Anggard E E. Probucol inhibits neointimal thickening and macrophage accumulation after balloon injury in the cholesterol-fed rabbit. Proc Natl Acad Sci USA 1992;89:11312-6.
29. Vermylen J. Clinical trials of primary and secondary prevention of thrombosis and restenosis. Thromb Haemost 1995;74:377-81.
30. Sarembock I J, Gertz S D, Thome L M, McCoy K W, Ragosta M, Power E R, Maraganore J M, Gimple L W. Effectiveness of hirulog in reducing restenosis after balloon angioplasty of atherosclerotic femoral arteries in rabbits. J Vas Res. 1996;33:308-14.
31. Gallo R, Padurean A, Toschi V, Bichler J, Fallon J T, Chesebro J H, Fuster V, Badimon J J. Prolonged thrombin inhibitor reduces restenosis after balloon angioplasty in porcine coronary arteries. Circ 1998;97:581-8.
32. Lefkovits J, Ivanhoe R J, Califf R M, Bergelson B A, Anderson K M, Stoner G L, Weisman H F, Topol E J. Effects of platelet glycoprotein IIb/IIIa receptor blockcade by a chimeric monoclonal antibody (abciximab) on acute and six-month outcomes after percutaneous transluminal coronary angioplasty for acute myocardial infarction. EPIC investigators. Am J Cardiol 19C6;77:1045-51.
33. Deitch J S, William J K, Admas M R, Fly C A, Herrington D M, Jordan R E, Nakada M T, Jakubowski J A, Geary R L. Effects of beta3-integrin blockade (c7E3) on the response to angioplasty and intra-arterial stenting in atherosclerotic nonhuman primates. Arterioscler Thromb Vasc Biol 1998; 18:1730-7.
34. McGregor M, Brophy J M. Use of anciximab (c7E3 Fab, ReoPro) as an adjunct to balloon angiography. Can J Cardiol 1999;15:201-7.
35. Hull R D, Pineo G F. Treatment of venous thromboembolism with low molecular weight heparins. Hematol/Oncol Clin North Am 1992;6:1095-103.
36. Study Design of the International Stroke Trial (IST), baseline, data and outcome in 984 randomised patients in the pilot study. J Neurol Neurosurg Psychiatry 1996;60: 371-6.
37. Weitz J I, Lesille B, Ginsberg J. Urokinase has direct catalytic activity against fibrinogen and renders it less clottable by thrombin. J Clin Invest 1990;86:385-91.
38. Au Y P T, Kenagy R D, Clowes A W. Heparin selectively inhibits the transcription of tissue-type plasminogen activator in primate arterial smooth muscle cells during mutagenesis. J Biol Chem 1991;267:3438-44.
39. Hirsh J, Weitz J I. New anti-coagulant agents. Lancet 1999;353:1431-6.
40. Gimple L W, Hermann H C, Winniford M, Mammen E. Usefulness of subcutaneous low molecular weight heparin (ardeparin) for reduction of restenosis after percutaneous transluminal coronary angioplasty. Am J Cardiol 1999;83: 1524-9.
41. Garabedian H D, Gold H K, Leinbach R C, Johns J A, Yasuda T, Kanke M, Collen D. Comparison properties of two clinical preparations of recombinant human tissue-type plasminogen activator in patients with acute myocardial infarction. Am Coll Cardiol 1987;9:599-607
42. Lavie C J, Gersh B J, Chesebro J H. Reperfusion in acute myocardial infarction. Mayo Clin Proc 1990;65:549-64
43. Harvery R P, Degryse E, Stefani L, Schamber F., Cazenave J P, Courtney M, Tolstoshev P, Lecocq J P. Cloning and expression of a cDNA coding for the anticoagulant hirudin from the bloodsucking leech, *hirudo medicinalis*. Proc Nat Acad Sci USA 1986;83:1084-8.
44. Serruys R W, Herrman J P R, Simon R, Ruston W, Bode C, Laarman G J, van Dijk R, van den Bos A A, Umans V A W M, Fox K A A, Close P, Deckers J W. A comparison or hirudin with heparin in the prevention of restenosis after coronary angioplasty. N Engl J. Med 1995;333:757-63.
45. Thome L M, Gimple L W, Bachhuber B G, McNamara C A, Ragosta M, Gertz S D, Powers E R, Owens G K, Humphries J E, Sarembock I J. Early and delayed hirudin reduces restenosis in the atherosclerotic rabbit more than ealy administration alone: potential implications for dosing of antithrombin agents. Circ 1998;98:2301-6.
46. Rade J J, Schulick A H, Virmani R, Dickek D A. Local adenoviral-mediated expression of recombinant hirudin reduces neointima formation after arterial injury. Nature-Med 1996;2:293-8.
47. van den Bos P, Deckers J W, Heyndrickx G R, Laarman G J, Suryapranata H, Zijistra F, Close P, Rijni J J, Butler H R, Serruys P W. Safety and efficacy of recombinant hirudin (CGP 39 393) versus heparin in patients with stable angina undergoing coronary angioplasty. Circ 1993;88: 2058-66.
48. Topol E J, Fuster V, Harrington R A, Califf R M, Kalian N S, Creaks D J, Cohen M, Chapekis A, Gold H K, Tannenbaum M A, Rae A K, Debone D, Schwartz D, Hanes M, Chesebro J. Recombinant hirudin for unstable angina pectoris. A multicenter, randomized angiographic trial. Circ 1994;89:1557-66.
49. Cannon C P, McCabe C H, Henry T D, Schwinger M J, Gibson R S, Mueller H S, Becker R C, Kalian N S, Haugland J M, Anderson J L, Sharaf B L, Edwards S J, Rogers W J, Williams D O, Braunwald E, for the TIMI5 Investigators. A pilot trial of recombinant desulfatohirudin compared with heparin in conjunction with tissue-type plasminogen activator and aspirin for acute myocardial infarction: results of the Thrombolysis in Myocardial Infarction (TIMI) 5 trial. J Am Coll Cardiol. 1994; 23:993-1003.
50. Lee L V, for the TIMI 6 Investigators. Initial experience with hirudin and streptokinase in acute myocardial infarction: Results of the thrombolysis in myocardial infarction (TIMI) 6 trial. Am J Cardiol. 1995;75:7-13.
51. Adgey A A. Bleeding complications with new antithrombotics used in ischaemic heart disease. Haemostasis. 1996; 26:237-46.
52. Antman E M, for the TIMI 9B Investigators. Hirudin in acute myocardial infarction thrombolysis and thrombin inhibition in myocardial (TIMI) 9B trial. Circ 1996;94: 911-21.
53. Global use of strategies to open occluded coronary arteries (GUSTO) IIa investigators heparin versus recombinant hirudin for acute coronary syndromes. Circ 1994 90:1624-30.
54. Neuhaus K L, von Essen R, Tebbe U, Jessel A, Heinrichs H, Maurer W, Doring W, Harmjanz D, Kotter V, Kalhammer E, Simon H, Horacek T. Safety observations from the pilot phase of the randomized r-Hirudin for Improvement of Thrombolysis (HIT-III) study. A study of the Arbeitsgemeinschaft Leitender Kardiologischer Krankenhausarzte (ALKK). Circ 1994;90:1638-42.
55. Maraganore J M, Bourdon P, Jablonski J, Ramachandran K L, Fenton J W II. Design and characterization of hirulogs: a novel class of bivalent peptide inhibitors of thrombin. Biochemistry 1990;29:7095-101.
56. Ofosu F A, Fenton J W II, Maraganore J, Blajchman M A, Yang X, Smith L, Anvari N, Buchanan M R, Hirsh J. Inhibition of the amplification reactions of blood coagulation by site specific inhibitions of $\alpha$-thrombin. Biochem J 1992;283:893-7
57. Lidon R M, Theroux P, Juneau M, Adelman B, Maraganore J. Initial experience with a direct antithrombin, Hirulog, in unstable angina. Anticoagulant, antithrombotic, and clinical effects. Circ 1993;88:1495-501.
58. Lidon R M, Theroux P, Lesperance J, Adelman B, Bonan R, Duval D, Levesque J. A pilot, early angiographic patency study using a direct thrombin inhibitor as adjunctive therapy to streptokinase in acute myocardial infarction. Circ. 1994;89:1567-72.
59. Bittl J A, Strony J, Brinker J A, Ahmed W H, Meckel C R, Chaitman B R, Maraganore J, Deutsch E, Adelman B. Treatment with bivalirudin (Hirulog) as compared with heparin during coronary angioplasty for unstable or postinfarction angina. Hirulog Angioplasty Study Investigators. N Engl J. Med. 1995;333:764-9.

60. Fenton J W II. Leeches to hirulogs and other thrombin-directed antithrombotics. Hematol Oncol Clin North Am. 1992; 6:1121-9.
61. Hamelink J K, Tang D B, Barr C F, Jackson M R, Reid T J, Gomez E R, Alving B M. Inhibition of platelet deposition by combined hirulog and aspirin in a rat carotid endarterectomy model. J Vas Surg. 1995;21:492-8.
62. Jackson M R, Reid T J Tang D B, O'Donnell S D, Gomez E R, Alving B M. Antithrombotic effects of hirulog in a rat carotid endarterectomy model. J Surg Res. 1996;60:15-22.
63. Muller D W, Gordon D, Topol E J, Levy R J, Golomb G. Sustained-release local hirulog therapy decreases early thrombosis but not neointimal thickening after arterial stenting. Am Heart J. 1996; 131:211-8.
64. Shen G, Xue M, Fenton J W II, Maraganore J M. Effect of hirulog-1 on fibrinolysis and platelet deposition. Atherosclerosis 1997; 134:195 (abstr).
65. Muller D W, Ellis S G, Topol E J. Experimental models of coronary artery restenosis J Am Coll Cardiol 1992;19:418-32.
66. Leveen R F, Wolf G L, Villanueva T G. New rabbit atherosclerotic model for the investigation transluminal angioplasty. Invest Radiol 1982;17:450-5.
67. Hehrlein C, Zimmermann M, Pill J, Metz J, Kubler W, von Hodenberg E. The role of elastic recoil after balloon angioplasty of rabbit arteries and its prevention by stent implantation. Eur Heart J 1994; 15:277-80.
68. Lafont A M, Chai Y C, Cornhill J F, Whitlow P L, Howe P H, Chisolm G M. Effect of alpha-tocopherol on restenosis after angioplasty in a model of experimental atherosclerosis. J Clin Invest 1995;95:1018-25.
69. Gal D, Rongione A J, Slovenkai G A, DeJesus S T, Lucas A, Fields C D, Isner J M. Atherosclerotic Yucatan microswine: an animal model with high-grade, fibrocalcific, nonfatty lesions suitable for testing catheter-based interventions. Am Heart J 1990;119:291-300.
70. Ferrell M, Fuster V, Gold H K, Chesebro J H. A dilemma for 1990s: choosing appropriate experimental animal model for the prevention of restenosis. Circ 1992;85:1630-1.
71. Clarkson T B, Hughes C L, Klein K P. The nonhuman primate model of the relationship between gonadal steroids and coronary heart disease. Prog Cardiovasc Dis 1995;38:189-98.
72. Verlangieri A J, Bush M J. Effects of d-alpha-tocopherol supplementation on experimentallyu induced primate atherosclerosis. J Am Coll Nutr 1992;11:131-8.
73. Wilcox J N, Harker L A, Kelly A B, Lumsden A B, Carey K D, Ollerenshaw J, Willis A L, Hanson S R. Inhibition of vascular lesion formation in the non-human primate using a chemically modified heparin derivatives, astenose™. Circ 1994;90(suppl I): 1-296. (abstr).
74. Camenzind E, Kint P P, Di Mario C, Ligthart J, van der Giessen W, Boersma E, Serruys P W. Intracoronary heparin delivery in humans. Acute feasibility and long-term results. Circ 1995;92:2463-72.
75. Wissler R W, Vesselinovitch D. Experimental models of human atherosclerosis. Ann NY Acad Sci 1966; 149:907-22.
76. Pratt R E, Dzau V J. Pharmacological strategies to prevent stenosis: lessons from blockage of renin-angiotensin system. Circ 1996;93:848-52.
77. Kritchevesky D, Tepper S A, Kim H K, Story J A, Vessekinovitvh D, Wissler R W. Experimental atherosclerosis in rabbits fed cholesterol-free diets 5. Comparison of peanut, corn, butter and coconut oils. Exp Mol Pathol 1976;24: 375-91.
78. Blajchman M A, Senyi A F, Hirsh J, Surya Y, Buchanan M, Mustard J F. Shorterning of the bleeding time in rabbits by hydrocortisone caused by inhibition of prostacyclin generation by the vessel wall. J Clin Invest 1979;63:1026-35.
79. Banai S, Wolf Y, Golomb G, Pearle A, Waltenberger J, Fishbein I, Schneider A, Gazit A, Perez L, Huber R, Lazarovichi G, Rabinovich L, Levitzki A, Gertz S D. PDGF-receptor tyrosine kinase blocker AG1295 selectively attenuates smooth muscle cell growth in vitro and reduced neointima formation after balloon angioplasty in swine. Circ 1998;97: 1960-9.
80. Huber K, Jorg M, Probst P, Schuster E, Lang T, Kaindl F, Binder B R. A decrease in plasminogen activator inhibitor-1 activity after successful percutaneous transluminal coronary angioplasty is associated with significant reduced risk for coronary restenosis. Thromb Haemost 1993;67: 209-13.
81. Halstead J, Kemp K, Ignotz R A. Evidence of involvement of phosphatidylcholine-phospholipase C and protein kinase C in transforming growth factor signaling. J Biol Chem 1995;270:13600-3.
82. Hansson G K, Seifert P S, Olsson G, Bondjers G. Immunohistochemidal detection of macrophages and T lymphocytes in atherosclerotic lesions of cholesterol-fed rabbits. Arterioscler Thromb 1991;11:745-50.
83. Wei G L, Krasinski K, Kearney M, Isner J M, Walsh K, Andres V. Temporally and spatially coordinated expression of cell cycle regulatory factors after angioplasty. Circ Res. 1997;80:418-26.
84. Soma M R, Natali M, Donetti E, Baetta R, Farina P, Leonardi A, Comparato C, Barberi L, Catapano A L. Effect of lercanidipine and its (R)-enantiomer on atherosclerotic lesions induced in hypercholesterolemic rabbits. Br J Pharmacol 1998;125:1471-6.
85. Cockell K A, Ren S, Sun J, Angel A, Shen G X. Effect of thrombin on release of plasminogen activator inhibitor-1 from cultured primate arterial smooth muscle cells. Thromb Res 1995;77:119-31.

What is claimed is:

1. A hirulog-like peptide comprising amino acids 1-32 of SEQ ID No. 1.

2. A method for treatment of vascular restenosis by reducing injury-induced neointima formation in an atherosclerotic mammal which method comprises providing a patient in need of treatment for restenosis an intravenous administration of an effective amount of a hirulog-like peptide (HLP) comprising amino acids 1-32 of SEQ ID No. 1.

3. A pharmaceutical composition comprising a hirulog-like peptide comprising amino acids 1-32 of SEQ ID No. 1 and a pharmaceutically acceptable carrier.

* * * * *

SEQUENCE LISTING

<160> NUMBER OF SEQ ID NOS: 2

<210> SEQ ID NO 1
<211> LENGTH: 32
<212> TYPE: PRT
<213> ORGANISM: artificial
<220> FEATURE:
<223> OTHER INFORMATION: synthetic peptide

```
-continued

<400> SEQUENCE: 1

Phe Pro Glu Ser Lys Ala Thr Asn Ala Thr Leu Asp Pro Arg Pro Gly
1               5                   10                  15

Gly Gly Gly Asn Gly Asp Phe Glu Glu Ile Pro Glu Glu Tyr Leu Gln
            20                  25                  30

<210> SEQ ID NO 2
<211> LENGTH: 20
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: D-phenylalanine

<400> SEQUENCE: 2

Phe Pro Arg Pro Gly Gly Gly Gly Asn Gly Asp Phe Glu Glu Ile Pro
1               5                   10                  15

Glu Glu Tyr Leu
            20
```